(12) United States Patent
Wallach et al.

(10) Patent No.: US 8,377,433 B2
(45) Date of Patent: Feb. 19, 2013

(54) SIVA 3, ITS PREPARATION AND USE

(75) Inventors: David Wallach, Rehovot (IL);
Parameswaran Ramakrishnan, Trivandrum (IN); Andrei Kovalenko, Andrei (IL)

(73) Assignee: Yeda Research and Development Co., Inc., Weizmann Institute of Science., Rehovot (IL)

( * ) Notice: Subject to any disclaimer, the term of this patent is extended or adjusted under 35 U.S.C. 154(b) by 2 days.

(21) Appl. No.: 12/866,593

(22) PCT Filed: Feb. 9, 2009

(86) PCT No.: PCT/IL2009/000151
§ 371 (c)(1),
(2), (4) Date: Aug. 6, 2010

(87) PCT Pub. No.: WO2009/098700
PCT Pub. Date: Aug. 13, 2009

(65) Prior Publication Data
US 2011/0035817 A1 Feb. 10, 2011

(30) Foreign Application Priority Data
Feb. 10, 2008 (IL) .......................................... 189408

(51) Int. Cl.
*A01N 63/02* (2006.01)
*C07H 21/04* (2006.01)
*C12N 5/10* (2006.01)
*C12N 15/12* (2006.01)

(52) U.S. Cl. ........ 424/93.7; 435/69.1; 435/325; 514/44; 536/23.5

(58) Field of Classification Search ................ 424/93.7; 435/69.1, 325; 514/44; 536/23.5
See application file for complete search history.

(56) References Cited

U.S. PATENT DOCUMENTS
2006/0216722 A1 9/2006 Betsholtz et al.

FOREIGN PATENT DOCUMENTS
| WO | WO 2005/051423 | * | 6/2005 |
| WO | 2007080593 A | | 7/2007 |
| WO | 2008067195 A | | 6/2008 |

OTHER PUBLICATIONS

Nestler et al, NM_006427.3, GI:119393886; Dec. 14, 2006.*
Heilig et al, AL583722.6; Jan. 16, 2006.*
Osoegawa et al, Genome Res. 11(3):483-496, 2001.*
Canicio, J., Ruiz-Lozano, P., Carrasco, M., Palacin, M., Chien, K., Zorzano, A., and Kaliman, P. (2001). Nuclear factor kappa B-inducing kinase and Ikappa B kinase-alpha signal skeletal muscle cell differentiation. J Biol Chem 276, 20228-20233.
Cao, C, Ren, X., Kharbanda, S., Koleske, A., Prasad, K. V., and Kufe, D. The ARG tyrosine kinase interacts with Siva-1 in the apoptotic response to oxidative stress. J Biol Chem 276, 11465-11468. 2001.
Chu, F., Barkinge, J., Hawkins, S., Gudi, R., Salgia, R., and Kanteti, P. V. Expression of Siva-1 protein or its putative amphipathic helical region enhances cisplatin-induced apoptosis in breast cancer cells: effect of elevated levels of BCL-2. Cancer Res 65, 5301-5309. 2005.
Chu, F., Borthakur, A., Sun, X., Barkinge, J., Gudi, R., Hawkins, S., and Prasad, K. V. The Siva-1 putative amphipathic helical region (SAH) is sufficient to bind to BCL-XL and sensitize cells to UV. Apoptosis (9):83-95, 2004.
Collins and Cybulsky, 2001. NF-kappaB: pivotal mediator or innocent bystander in atherogenesis? J Clin Invest. 107 (3):255-64.
Deng, L., Wang, C, Spencer, E., Yang, L, Braun, A., You, J., Slaughter, C, Pickart, C, and Chen, Z. J. Activation of The IkappaB kinase complex by TRAF6 requires a dimeric ubiquitin-conjugating enzyme complex and a unique polyubiquitin chain. Cell 103, 351-361. 2000.
Dorsett, Y. and T. Tuschl (2004). "siRNAs: applications in functional genomics and potential as therapeutics." Nature Reviews Drug Discov 3(4): 318-29.
Edinger et al. 1998 Use of GPR1, GPR15, and STRL33 as coreceptors by diverse human immunodeficiency virus type 1 and simian immunodeficiency virus envelope proteins. Virology. Sep. 30, 1998;249(2):367-78.
Fanslow, W. C, Clifford, K. N., Seaman, M., Alderson, M. R., Spriggs, M. K., Armitage, R. J., and Ramsdell, F. Recombinant CD40 ligand exerts potent biologic effects on T cells. J Immunol 152, 4262-4269. 1994.
Foehr, E.D. et al., 2000. The NF-kappaB-inducing Kinase Induces PC12 Cell Differntiation and Prevents Apoptosis. J Biol Chem. 275:34021-4.
Fontanari Krause et al, The OSTL Gene Encodes for a Conserved RING Finger Protein Which Interacts with HAX1 and SIVA: Possible Role in B Cell Signaling and Survival. Abstract 3152, Blood, vol. 102, 11, Nov. 16, 2003.
Fortin, A., MacLaurin, J. G., Arbour, N., Cregan, S. P., Kushwaha, N., Callaghan, S. M., Park, D. S., Albert, P. R., and Slack, R. S. The proapoptotic gene SIVA is a direct transcriptional target for the tumor suppressors p. 53 and E2F1. J Biol Chem 279, 28706-28714. 2004.
Glickman, M. H., and Ciechanover, A. The ubiquitin-proteasome proteolytic pathway: destruction for the sake of construction. Physiol Rev 82, 373-428. 2002.
Grech, A. P., Amesbury, M., Chan, T., Gardam, S., Basten, A., and Brink, R. TRAF2 differentially regulates the canonical and noncanonical pathways of NF-kappaB activation in mature B cells. Immunity 21, 629-642. 2004.
Hemmi et al. 1998 the Presence of Human Coxsackievirus and Adenovirus Receptor Is Associated with Efficient Adenovirus-Mediated Transgene Expression in Human Melanoma Cell Cultures. Hum Gene Ther. Nov. 1, 1998;9 (16):2363-73.
Henke, A., Launhardt, H., Klement, K., Stelzner, A., Zell, R., and Munder, T. Apoptosis in coxsackievirus B3-caused diseases: interaction between the capsid protein VP2 and the proapoptotic protein siva. J Virol 74, 4284-4290. 2000.
Hofmann, K., and Falquet, L. A ubiquitin-interacting motif conserved in components of the proteasomal and lysosomal protein degradation systems. Trends Biochem Sci 26, 347-350. 2001.

(Continued)

*Primary Examiner* — Kevin K. Hill
(74) *Attorney, Agent, or Firm* — Nixon Peabody LLP; David S. Resnick; Leena H. Karttunen Contarino

(57) ABSTRACT

The present invention relates to a splice variant of SIVA, SIVA3, and to its use.

7 Claims, 4 Drawing Sheets

OTHER PUBLICATIONS

Hofmann, R. M., and Pickart, C. M. In vitro assembly and recognition of Lys-63 polyubiquitin chains. J Biol Chem 276, 27936-27943. 2001.

Kajiura, F., Sun, S., Nomura, T., Izumi, K., Ueno, T., Bando, Y., Kuroda, N., Han, H., Li, Y., Matsushima, A., et al. (2004). NF-kappa B-inducing kinase establishes self-tolerance in a thymic stroma-dependent manner. J Immunol 172, 2067-2075.

Karin, M., and Ben-Neriah, Y. Phosphorylation meets ubiquitination: the control of NF-[kappa]B activity. Annu Rev Immunol 18, 621-663. 2000.

Kim, D. H., M. A. Behlke, et al. (2005). "Synthetic dsRNA Dicer substrates enhance RNAi potency and efficacy." Nature Biotechnol 23(2): 222-6.

Kovalenko, A., Chable-Bessia, C, Cantarella, G., Israel, A., Wallach, D., and Courtois, G. The tumour suppressor CYLD negatively regulates NF-kappaB signalling by deubiquitination. Nature 424, 801-805. 2003.

Lee, Z. H., Lee, S. E., Kwack, K., Yeo, W., Lee, T. H., Bae, S. S., Suh, P. G., and Kim, H. H. Caspase-mediated cleavage of TRAF3 in FasL-stimulated Jurkat-T cells. J Leukoc Biol 69, 490-496. 2001.

Leonard, W.J. et al., 1995. Role of the Common Cytokine Receptor gamma Chain in Cytokine Signaling and Lymphoid Development. Immunol Rev. 148:97-114.

Liao, G., Zhang, M., Harhaj, E. W., and Sun, S. C. Regulation of the NF-kappaB-inducing kinase by tumor necrosis factor receptor-associated factor 3- induced degradation. J Biol Chem 279, 26243-26250. 2004.

Lin, X. et al., 1999. The Proto-Oncogene Cot Kinase Participates in CD3/CD28 Induction of NF-kappaB Acting through the NF-kappaB-Inducing Kinase and IkappaB Kinases. Immunity 10:271-80.

Ling, L. et al., 1998. NF-kappaB-inducing kinase activates IKK-alpha by phosphorylation of Ser-176. Proc Natl Acad Sci U S A. 95:3792-7.

Lois, C, Hong, E. J., Pease, S., Brown, E. J., and Baltimore, D. Germline transmission and tissue-specific expression of transgenes delivered by lentiviral vectors. Science 295, 868-872. 2002.

Malinin, N. L., Boldin, M. P., Kovalenko, A. V., and Wallach, D. MAP3K—related kinase involved in NF-kappaB induction by TNF, CD95 and IL-I . Nature 385, 540-544. 1997.

Matsumoto, M. et al., 1999. Involvement of Distinct Cellular Compartments in the Abnormal Lymphoid Organogenesis in Lymphotoxin-alpha-Deficient Mice and Alymphoplasia (aly) Mice Defined by the Chimeric Analysis. J Immunol. 163:1584-91.

Matsushima, A. et al., 2001. Essential Role of Nuclear Factor (NF)-kappaB-inducing Kinase and Inhibitor of kappaB (IkappaB) Kinase alpha in NF-kappaB Activation through Lymphotoxin beta Receptor, but Not through Tumor Necrosis Factor Receptor I. J Exp Med. 193:631-6.

Mattson and Camandola, 2001. NF-kappaB in neuronal plasticity and neurodegenerative disorders. J Clin Invest. 107:247-54.

Mercurio F. and Manning A.M., 1999. Multiple signals converging on NF-kappaB. Curr Opin Cell Biol. 11:226-32.

Miyawaki, S., Nakamura, Y., Suzuka, H., Koba, M., Yasumizu, R., Ikehara, S., and Shibata, Y. (1994). A new mutation, aly, that induces a generalized lack of lymph nodes accompanied by immunodeficiency in mice. Eur J Immunol 24, 429-434.

Muranishi et al., 1991 Lipophilic peptides: synthesis of lauroyl thyrotropin-releasing hormone and its biological activity .Pharm Res. May 1991;8(5):649-52.

Nocentini, G., and Riccardi, C. GITR: a multifaceted regulator of immunity belonging to the tumor necrosis factor receptor superfamily. Eur J Immunol 35, 1016-1022. 2005.

Padanilam, B. J., Lewington, A. J., and Hammerman, M. R. Expression of CD27 and ischemia/reperfusion-induced expression of its ligand Siva in rat kidneys. Kidney Int 54, 1967-1975. 1998.

Petit PX, P. B., Mrugala D, Biard-Piechaczyk M, Benichou S.SIVA: A new intracellular ligand of the CD4 receptor modulating T lymphocyte apoptosis via a caspase-dependent mitochondrial pathway, Paper presented at: ISAC congress XXII (France: Wiley-Liss, DIV John Wiley & Sons Inc, 11 1 River St) Hoboken, NJ 07030 USA). 2004.

Pickart, C. M. Mechanisms underlying ubiquitination. Annu Rev Biochem 70, 503-533. 2001.

Pomerantz, J. L., and Baltimore, D. (2002). Two pathways to NF-kappaB. Mol Cell 10, 693-695.

Prasad, K. V., Ao, Z., Yoon, Y., Wu, M. X., Rizk, M., Jacquot, S., and Schlossman, S. F. (1997). CD27, a member of the tumor necrosis factor receptor family, induces apoptosis and binds to Siva, a proapoptotic protein. Proc Natl Acad Sci U S A 94, 6346-6351.

Py, B., Slomianny, C, Auberger, P., Petit, P. X, and Benichou, S. Siva-1 and an alternative splice form lacking the death domain, Siva-2, similarly induce apoptosis in T lymphocytes via a caspasedependent mitochondrial pathway. J Immunol 172, 4008-4017. 2004.

Qin, L. F., Lee, T. K., and Ng, I. O. Gene expression profiling by cDNA array in human hepatoma cell line in response to cisplatin treatment. Life Sci 70, 1677-1690. 2002.

Ramakrishnan, P., Wang, W., and Wallach, D. Receptor-specific signaling for both the alternative and the canonical NF-kappaB activation pathways by NF-kappaB-inducing kinase. Immunity 21 , 477-489. 2004.

Regnier, C.H. et al., 1997. Identification and Characterization of an IkappaB Kinase. Cell 90:373-83.

Rigaut, G., Shevchenko, A., Rutz, B., Wilm, M., Mann, M., and Seraphin, B. A generic protein purification method for protein complex characterization and proteome exploration. Nature Biotechnol 17, 1030-1032. 1999.

Database Geneseq [Online] Jan. 11, 2007, "Human apoptosis regulatory protein Siva gene, SEQ ID No. 901." XP002530828 retrieved from EBI accession No. GSN:AEL56438, Database accession No. AEL56438 (in connection with US Publ. No. 20060216722).

Database Geneseq [Online] Jan. 11, 2007, "Human apoptosis regulatory protein Siva gene, SEQ ID No. 903." XP002530829 retrieved from EBI accession No. GSN:AEL56440, Database accession No. AEL56440. (in connection with US Publ. No. 20060216722).

Database Geneseq [Online] Jan. 11, 2007, "Human apoptosis regulatory protein Siva, SEQ ID No. 902." XP002530830 retrieved from EBI accession No. GSP:AEL56439, Database accession No. AEL56439. (in connection with US Publ. No. 20060216722).

Database Geneseq [Online] Jan. 11, 2007, "Human apoptosis regulatory protein Siva, SEQ ID No. 904. GCAVVHLPES PKPGPTGAPR AARGQMLIGP DGRLIRSLGQ ASEADPSGVA SIACSSCVRA." XP002530831 retrieved from EBI accession No. GSP:AEL56441, Database accession No. AEL56441. (in connection with US Publ. No. 20060216722).

Database Geneseq [Online] Nov. 1, 2007, "Human SIVA2 N-terminal polypeptide (aa1-58)." XP002530832 retrieved from EBI accession No. GSP:AGV38712, Database accession No. AGV38712. (in connection with WO Publ. No. 2007080593).

Database Geneseq [Online] Nov. 1, 2007, "Human SIVA2 N-terminal polypeptide (aa1-81)." XP002530833 retrieved from EBI accession No. GSP:AGV38713, Database accession No. AGV38713. (in connection with WO Publ. No. 2007080593).

Database Geneseq [Online] Nov. 1, 2007, "Human SIVA2 protein." XP002530834 retrieved from EBI accession No. GSP:AGV38710, Database accession No. AGV38710. (in connection with WO Publ. No. 2007080593).

Database Geneseq [Online] Nov. 1, 2007, "Human SIVA1 protein. GCAVVHLPES PKPGPTGAPR AARGQMLIGP ASEADPSGVA SIACSSCVRA" XP002530835 retrieved from EBI accession No. GSP: AGV38709, Database accession No. AGV38709. (in connection with WO Publ. No. 2007080593).

Database Geneseq [Online] Nov. 13, 2008, "Crohn's disease associated polypeptide SEQ ID No. 8729." XP002530824 retrieved from EBI accession No. GSP:ATK98104, Database accession No. ATK98104. (in connection with WO Publ. No. 2008067195).

Database Geneseq [Online] Nov. 13, 2008, "Crohn's disease associated polypeptide SEQ ID No. 8713." XP002530825 retrieved from EBI accession No. GSP:ATK98088, Database accession No. ATK98088. (in connection with WO Publ. No. 2008067195).

Database Geneseq [Online] Nov. 13, 2008, "Crohn's disease associated polynucleotide SEQ ID No. 8728." XP002530826 retrieved from EBI accession No. GSP:ATK98103, Database accession No. ATK98103. (in connection with WO Publ. No. 2008067195).

Database Geneseq [Online] Nov. 13, 2008, "Crohn's disease associated polynucleotide SEQ ID No. 8718." XP002530827 retrieved from EBI accession No. GSP:ATK98093, Database accession No. ATK98093. (in connection with WO Publ. No. 2008067195).

Prasad KV et al., "CD27, a member of the tumor necrosis factor receptor family, induces apoptosis and binds to Siva, a proapoptotic protein." Proc Natl Acad Sci U S A. 94(12):6346-6351, 1997.

Ramakrishnan P et al., "Receptor-specific signaling for both the alternative and the canonical NF-kappaB activation pathways by NF-kappaB-inducing kinase." Immunity 21(4):477-489, 2004.

Py B et al., "Siva-1 and an alternative splice form lacking the death domain, Siva-2, similarly induce apoptosis in T lymphocytes via a caspase-dependent mitochondrial pathway." J Immunol 172(7):4008-4017, 2004.

Schreiber, E., Matthias, P., Muller, M. M., and Schaffner, W. Rapid detection of octamer binding proteins with 'mini-extracts', prepared from a small number of cells. Nucleic Acids Res 17, 6419. 1989.

Senftleben, U., Cao, Y., Xiao, G., Greten, F. R., Krahn, G., Bonizzi, G., Chen, Y., Hu, Y., Fong, A., Sun, S. C, and Karin, M. Activation by IKKalpha of a second, evolutionary conserved, NF-kappa B signaling pathway. Science 293, 1495-1499. 2001.

Shinkura, R., Kitada, K., Matsuda, F., Tashiro, K., Ikuta, K., Suzuki, M., Kogishi, K., Serikawa, T., and Honjo, T. Alymphoplasia is caused by a point mutation in the mouse gene encoding Nf-kappa binducing kinase. Nat Genet 22, 74-77.107. 1999.

Soutschek, J., A. Akinc, et al. (2004). "Therapeutic silencing of an endogenous gene by systemic administration of modified siRNAs." Nature 432(7014): 173-8.

Spinicelli, S., Nocentini, G., Ronchetti, S., Krausz, L. T., Bianchini, R., and Riccardi, C. GITR interacts with the pro-apoptotic protein Siva and induces apoptosis. Cell Death Differ 9, 1382-1384. 2002.

Sylla, B.S. et al., 1998. Epstein-Barr virus-transforming protein latent infection membrane protein 1 activates transcription factor NF-kappaB through a pathway that includes the NF-kappaB-inducing kinase and the IkappaB kinases IKKalpha and IKKbeta. Proc Natl Acad Sci U S A. 95:10106-11.

Wajant, H., and Scheurich, P. (2003). Analogies between Drosophila and mammalian TRAF pathways. Prog Mol Subcell Biol 34, 47-72.

Wang and Low, 1998 Folate-mediated targeting of antineoplastic drugs, imaging agents, and nucleic acids to cancer cells. J Control Release. Apr. 30, 1998;53(1-3):39-48. Review.

Xiao, G., and Sun, S. C. Negative regulation of the nuclear factor kappa B- inducing kinase by a cis-acting domain. J Biol Chem 275, 21081-21085. 2000.

Xiao, G., Fong, A., and Sun, S. C. Induction of plOO processing by NF- kappaB-inducing kinase involves docking IkappaB kinase alpha (IKKalpha) to p100 and IKKalpha-mediated phosphorylation. J Biol Chem 279, 30099-30105. 2004.

Xu, L. G., Li, L. Y., and Shu, H. B. (2004). TRAF7 potentiates MEKK3-induced API and CHOP activation and induces apoptosis. J Biol Chem 279, 17278-17282.

Xue, L, Chu, F., Cheng, Y., Sun, X, Borthakur, A., Ramarao, M., Pandey, P., Wu, M., Schlossman, S. F.,and Prasad, K. V. Siva-1 binds to and inhibits BCL-X(L)-mediated protection against UV. Proc. Natl. Acad. Sci. USA 99 (10):6925-6930, 2002.

Yamamoto and Gaynor, 2001. Therapeutic potential of inhibition of the NF-kappaB pathway in the treatment of inflammation and cancer. J Clin Invest. 107:135-142.

Yoon, Y., Ao, Z., Cheng, Y., Schlossman, S. F., and Prasad, K. V. Murine Siva-1 and Siva-2, alternate splice forms of the mouse Siva gene, both bind to CD27 but differentially transduce apoptosis. Oncogene 18, 7174-7179. 1999.

Zacharia et al. 1991 New reduced peptide bond substance P agonists and antagonists: effects on smooth muscle contraction. Eur J Pharmacol. Oct. 22, 1991;203(3):353-7.

Zhang et al. "Expression of Potential Target Antigens for Immunotherapy on Primary and Metastatic Prostate Cancers." Clin Cancer Res. Feb. 1998;4(2):295-302.

* cited by examiner

ATGCCCAAGCGGAGCTGCCCCTTCGCGGACGTGGCCCCGCTACAGCTCAAGGTCCGCGTGAGCCAGAGGGAGTTGAGCCG
CGGCGTGTGCGCCGAGCGCTACTCGCAGGAGGTCTTCGCAGTGACATGTACGAGAAAGTGTGCACCAGCTGTGC
CATGTTCGAGACCTGAGGCTGGCTCAAGCCGGCTCACCGGAGCCACGCCGTGCATGGCAGCCTTCCCTGGACGA
GCGCTCGGTGTTCACACTGAACTGTGGGGTCGACGGGAGGGGTGCCTTTACATGTTCTATTTGTATCCTAATGACAGA
ATGA

FIG. 2

MPKRSCPFADVAPLQLKVRVSQRELSRGVCAERYSQEVFAAVTCTRKCCAPAVPCSRPEAGSSRLPSPGATPCMAAFPGR
ALGVHTELWGRREGCLLHVLFCILMTE

FIG. 3

SIVA 3, ITS PREPARATION AND USE

CROSS REFERENCE TO RELATED APPLICATIONS

This application is a National Phase Entry Application under 35 U.S.C. §371 of co-pending International Application PCT/IL2009/000151, filed 9 Feb. 2009, which claims benefit of Israeli application No. 189408, filed on 10 Feb. 2008.

SEQUENCE LISTING

The instant application contains a Sequence Listing which has been submitted in ASCII format via EFS-Web and is hereby incorporated by reference in its entirety. Said ASCII copy, created on Sep. 11, 2012, is named 057878US.txt and is 3,532 bytes in size.

FIELD OF THE INVENTION

The present invention relates to a splice variant of SIVA, SIVA3, and to its use.

BACKGROUND OF THE INVENTION

Members of the TNF/NGF receptor family are expressed in almost all types of cells and control a wide range of diverse cellular activities. They have the ability both to induce cellular changes that are protein-synthesis independent, the best known of which is caspase-mediated cell death (the extrinsic cell-death pathway), and to modulate gene-expression patterns both on the transcriptional and the post-transcriptional levels. These effects contribute to the control of practically all aspects of immune defense as well as some embryonic-development and tissue-homeostatic processes. They vary, and depending on the type of cell and the identity of the activated receptor, as well as on numerous other determinants, some effects might even oppose others. This wide range of activities is mediated by a rather small number of signaling proteins, of which the best characterized are two death-domain-containing adapters, FADD/MORT1 and TRADD, the inducer caspases caspase-8 and -10, members of the TRAF ring-finger proteins, and cellular inhibitor of apoptosis protein 1 (cIAP1) and cIAP2 (ring-finger proteins with IAP motifs) (Wallach et al., Annu Rev Immunol. 1999;17:331-67. Review.) (Locksley et al., Cell. 2001 Feb. 23; 104(4):487-501.). How this limited set of proteins mediates the multiplicity of different effects of the receptors, and how the nature of the induced effect is adjusted to need, are still poorly understood.

SIVA, an additional protein suggested to participate in the proximal signaling activities of members of the TNF/NGF receptor family, was identified by virtue of its binding to the receptor CD27 in the yeast two-hybrid test (Prasad et al., 1997). Some evidence was also presented for its association with several other members of the TNF/NGF receptor family (Nocentini and Riccardi, 2005). The existence of SIVA has been known for some years, and it was shown that when overexpressed for prolonged periods this protein kills cells (Prasad et al., 1997). However, whether this is its genuine and sole activity is not known. SIVA shows no close structural resemblance to any other known protein. One region within it that initially appeared to resemble the death domain does not contain the structural signatures by which that domain is characterized. C-terminally to that region the protein is relatively enriched in cysteine residues, which apparently contribute to its binding of several zinc ions (Nestler et al., 2006). The amino-acid sequence in this region, however, does not strictly conform to any of the known zinc-binding motifs. A central short α-helical region in the protein binds the anti-apoptotic protein BCL-$X_L$ (Xue et al., 2002), but the function served by the cysteine-rich region (CRR) is unknown.

SIVA it is known to exist as two alternative splice isoforms or splice variants, SIVA1 and SIVA2. SIVA1 is longer and contains a death domain homology region (DDHR) with a putative amphipathical helix in its central part. SIVA2 is shorter and lacks the DDHR. Both isoforms contain a B-box-like ring finger and a Zinc finger like domain in their C-termini. Enforced expression of both SIVA1 and SIVA2 has been shown to induce apoptosis (Prasad et al., 1997, Yoon et al., 1998, Spinicelli et al., 2003, (Py et al., 2004). SIVA1 induced apoptosis is suggested to be effected by its binding to and inhibition of the anti apoptotic Bcl-2 family members through its amphipathic helical region (Chu et al., 2005; Chu et al., 2004; Xue et al., 2002). Consistent with its pro-apoptotic role, SIVA is a direct transcriptional target for tumor suppressors p53 and E2F1 (Fortin et al., 2004). Various point of evidence indicate that SIVA is a stress-induced protein and is up-regulated in acute ischemic injury (Padanilam et al., 1998), coxavirus infection (Henke et al., 2000), and also by cisplatin treatment (Qin et al., 2002), as well as TIP30 expression which induces apoptosis (Xiao et al., 2000). Recently, the common N- and C-termini of SIVA1 and SIVA2, yet not the death domain, have been shown to be sufficient and capable to mediate apoptosis in lymphoid cells through activation of a caspase dependent mitochondrial pathway (Py et al., 2004).

Recently, it was found that SIVA binds to NF-κB-inducing kinase (NIK) and controls its function (Ramakrishnan et al., 2004), has ubiquitination-related activity, is capable of directly inducing self-ubiquitination, ubiquitination of TRAF2 (a TNF-receptor associated adaptor protein 2), and that SIVA2 is an E3 ligase (WO2007080593).

Ubiquitylation, also termed ubiquitination, refers to the process particular to eukaryotes whereby a protein is post-translationally modified by covalent attachment of a small protein named ubiquitin [originally ubiquitous immunopoeitic polypeptide (UBIP)]. Ubiquitin ligase is a protein which covalently attaches ubiquitin to a lysine residue on a target protein. The ubiquitin ligase is typically involved in poly-ubiquitylation: a second ubiquitin is attached to the first, a third is attached to the second, and so forth. The ubiquitin ligase is referred to as an "E3" and operates in conjunction with an ubiquitin-activating enzyme (referred herein as "E1") and an ubiquitin-conjugating enzyme (referred herein as "E2"). There is one major E1 enzyme, shared by all ubiquitin ligases, which uses ATP to activate ubiquitin for conjugation and transfers it to an E2 enzyme. The E2 enzyme interacts with a specific E3 partner and transfers the ubiquitin to the target protein. The E3, which may be a multi-protein complex, is generally responsible for targeting ubiquitination to specific substrate proteins. In some cases it receives the ubiquitin from the E2 enzyme and transfers it to the target protein or substrate protein; in other cases it acts by interacting with both the E2 enzyme and the substrate.

NIK, (MAP3K14) was discovered (Malinin et al., 1997) in a screening for proteins that bind to TRAF2. The marked activation of NF-κB upon overexpression of NIK, and effective inhibition of NF-κB activation in response to a variety of inducing agents, upon expression of catalytically inactive NIK mutants suggested that NIK participates in signaling for NF-κB activation (Malinin et al., 1997).

Assessment of the pattern of the NF-κB species in lymphoid organs indicated that, apart from its role in the regulation of NF-κB complex(s) comprised of Rel proteins and IκB, NIK also participates in controlling the expression/activation of other NF-78 B species. Indeed, NIK has been shown to participate in site-specific phosphorylation of p100, which serves as a molecular trigger for ubiquitination and active processing of p100 to form p52. This p100 processing activity was found to be ablated by the aly mutation of NIK (Xiao et al., 2001b).

NIK in thymic stroma is important for the normal production of Treg cells, which are essential for maintaining immunological tolerance. NIK mutation resulted in disorganized thymic structure and impaired production of Treg cells in aly mice (Kajiura et al., 2004). Consistently, studies of NIK-deficient mice also suggested a role for NIK in controlling the development and expansion of Treg cells (Lu et al., 2005). These findings suggest an essential role of NIK in establishing self-tolerance in a stromal dependent manner. NIK also partakes in NF-κB activation as a consequence of viral infection. Respiratory syncytial virus infection results in increased kinase activity of NIK and the formation of a complex comprised of activated NIK, IKK1, p100 and the processed p52 in alveolus like a549 cells. In this case NIK itself gets translocated into the nucleus bound to p52 and surprisingly, these events precede the activation of canonical NF-κB pathway activation (Choudhary et al., 2005). These findings indicate that NIK indeed serves as a mediator of NF-κB activation, but may also serve other functions, and that it exerts these functions in a cell- and receptor-specific manner.

NIK can be activated as a consequence of phosphorylation of the 'activation loop' within the NIK molecule. Indeed, mutation of a phosphorylation-site within this loop (Thr-559) prevents activation of NF-κB upon NIK overexpression (Lin et al., 1999). In addition, the activity of NIK seems to be regulated through the ability of the regions upstream and downstream of its kinase motif to bind to each other. The C terminal region of NIK downstream of its kinase moiety has been shown to be capable of binding directly to IKK1 (Regnier et al., 1997) as well as to p100 (Xiao et al., 2001b) and these interactions are apparently required for NIK function in NF-κB signaling. The N terminal region of NIK contains a negative-regulatory domain (NRD), which is composed of a basic motif (BR) and a proline-rich repeat motif (PRR) (Xiao and Sun, 2000). The N-terminal NRD interacts with the C-terminal region of NIK in cis, thereby inhibiting the binding of NIK to its substrate (IKK1 and p100). Ectopically expressed NIK spontaneously forms oligomers in which these bindings of the N-terminal to the C terminal regions in each NIK molecule are apparently disrupted, and display a high level of constitutive activity (Lin et al., 1999). The binding of the NIK C-terminal region to TRAF2 (as well as to other TRAF's) most likely participates in the activation process. However, its exact mode of participation is unknown.

Recently, a novel mechanism of NIK regulation has gained much attention. This concerns the dynamic interaction of NIK and TRAF3 leading to proteasome mediated degradation of NIK. Interestingly, inducers of the alternative pathway of NF-κB like CD40 and BLyS have been shown to induce TRAF3 degradation and concomitant enhancement of NIK expression (Liao et al., 2004).

There is rather limited information yet of the downstream mechanisms in NIK action. Evidence has been presented that NIK, through the binding of its C-terminal region to IKK1 can activate the IKB kinase (IKK) complex. It has indeed been shown to be capable of phosphorylating serine-176 in the activation loop of IKK1 and thereby its activation (Ling et al., 1998).

It was suggested that NIK does not participate at all in the canonical NF-κB pathway, but rather serves exclusively to activate the alternative one (see (Pomerantz and Baltimore, 2002, for review). However, it was lately shown that although the induction of IkappaB degradation in lymphocytes by TNF is independent of NIK, its induction by CD70, CD40 ligand, and BLyS/BAFF, which all also induce NF-kappaB2/p 100 processing, does depend on NIK function (Ramakrishnan et al. 2004). Both CD70 and TNF induce recruitment of the IKK kinase complex to their receptors. In the case of CD70, but not TNF, this process is associated with NIK recruitment and is followed by prolonged receptor association of just IKK1 and NIK. Recruitment of the IKK complex to CD27, but not that of NIK, depends on NIK kinase function. These findings indicate that NIK participates in a unique set of proximal signaling events initiated by specific inducers, which activate both canonical and noncanonical NF-kappaB dimers.

Yamamoto and Gaynor reviewed the role of NF-κB in pathogenesis of human disease (Yamamoto and Gaynor 2001). Activation of the NF-κB pathway is involved in the pathogenesis of chronic inflammatory disease, such as asthma, rheumatoid arthritis (see Tak and Firestein, this Perspective series, ref. Karin et al. 2000), and inflammatory bowel disease. In addition, altered NF-κB regulation may be involved in other diseases such as atherosclerosis (see Collins and Cybulsky, this series, ref. Leonard et al. 1995) and Alzheimer's disease (see Mattson and Camandola, this series, ref. Lin et al. 1999), in which the inflammatory response is at least partially involved. Also, abnormalities in the NF-κB pathway are also frequently seen in a variety of human cancers.

Several lines of evidence suggest that NF-κB activation of cytokine genes is an important contributor to the pathogenesis of asthma, which is characterized by the infiltration of inflammatory cells and the deregulation of many cytokines and chemokines in the lung (Ling et al. 1998). Likewise, activation of the NF-κB pathway also likely plays a role in the pathogenesis of rheumatoid arthritis. Cytokines, such as TNF-, that activate NF-κB are elevated in the synovial fluid of patients with rheumatoid arthritis and contribute to the chronic inflammatory changes and synovial hyperplasia seen in the joints of these patients (Malinin et al. 1997). The administration of antibodies directed against TNF- or a truncated TNF-receptor that binds to TNF- can markedly improve the symptoms of patients with rheumatoid arthritis.

Increases in the production of proinflammatory cytokines by both lymphocytes and macrophages have also been implicated in the pathogenesis of inflammatory bowel diseases, including Crohn's disease and ulcerative colitis (Matsumoto et al. 1999). NF-κB activation is seen in mucosal biopsy specimens from patients with active Crohn's disease and ulcerative colitis. Treatment of patients with inflammatory bowel diseases with steroids decreases NF-κB activity in biopsy specimens and reduces clinical symptoms. These results suggest that stimulation of the NF-κB pathway may be involved in the enhanced inflammatory response associated with these diseases.

Atherosclerosis is triggered by numerous insults to the endothelium and smooth muscle of the damaged vessel wall (Matsushima et al. 2001). A large number of growth factors, cytokines, and chemokines released from endothelial cells, smooth muscle, macrophages, and lymphocytes are involved in this chronic inflammatory and fibroproliferative process (Matsushima et al. 2001). NF-□B regulation of genes involved in the inflammatory response and in the control of cellular proliferation likely plays an important role in the initiation and progression of atherosclerosis.

Also, abnormalities in the regulation of the NF-κB pathway may be involved in the pathogenesis of Alzheimer's disease. For example, NF-κB immunoreactivity is found predominantly in and around early neuritic plaque types in Alzheimer's disease, whereas mature plaque types show vastly reduced NF-☐B activity (Mercurio et al. 1999). Thus, NF-κB activation may be involved in the initiation of neuritic plaques and neuronal apoptosis during the early phases of Alzheimer's disease. These data suggest that activation of the NF-κB pathway may play a role in a number of diseases that have an inflammatory component involved in their pathogenesis.

In addition to a role in the pathogenesis of diseases characterized by increases in the host immune and inflammatory response, constitutive activation of the NF-κB pathway has also been implicated in the pathogenesis of some human cancers. Abnormalities in the regulation of the NF-κB pathway are frequently seen in a variety of human malignancies including leukemias, lymphomas, and solid tumors (Miyawaki et al. 1994). These abnormalities result in constitutively high levels of NF-κB in the nucleus of a variety of tumors including breast, ovarian, prostate, and colon cancers. The majority of these changes are likely due to alterations in regulatory proteins that activate signaling pathways that lead to activation of the NF-κB pathway. However, mutations that inactivate the I B proteins in addition to amplification and rearrangements of genes encoding NF-κB family members can result in the enhanced nuclear levels of NF-κB seen in some tumors.

Apart from the contribution to the regulation of the development and function of the immune system, NIK seems also to be involved in the regulation of various non-immune functions such as mammary gland development (Miyawaki et al., 1994). NIK has a role in lymphoid organ development (Shinkura et al., 1999). In vitro studies implicated NIK in signaling that leads to skeletal muscle cell differentiation (Canicio et al., 2001), and in the survival and differentiation of neurons (Foehr et al., 2000).

A need of a satisfactory treatment exists for numerous lethal and/or highly debilitating diseases associated with disregulated activity of NIK and/or NF-.κ.B molecules, including malignant diseases and diseases associated with pathological immune responses, such as autoimmune, allergic, inflammatory, and transplantation-related diseases.

SUMMARY OF THE INVENTION

In one aspect, the invention relates to an isolated polynucleotide selected from (a) a polynucleotide encoding SIVA3 comprising the amino acid sequence set forth in SEQ ID NO: 1 (FIG. 3); or a mutein; isoform; fused protein; functional derivative; fragment, active fraction; or circularly permutated derivative thereof; (b) a polynucleotide comprising a sequence capable of hybridizing under moderately stringent conditions to a polynucleotide sequence spanning nucleotides 119 to 324 of SEQ ID NO: 2 or to a fragment thereof (c) a polynucleotide comprising at least 10, 11-29, 30-50, and 50-199 consecutive nucleotides, and a fragment of 200-205 consecutive nucleotides from a polynucleotide sequence comprised from 119 to 324 of SEQ ID NO: 2 (d) a clone of deposit number CNCM 1-3880 having the sequence of SEQ ID NO: 2 (FIG. 2).

In one embodiment, the invention relates to a polynucleotide comprising the sequence set forth in SEQ ID NO: 2.

In another embodiment of the invention, the polynucleotide comprises a sequence capable of hybridizing under moderately stringent conditions to a polynucleotide sequence from 119 to 324 of SEQ ID NO: 2 or to a fragment thereof wherein said polynucleotide is a SIVA3 specific ribozyme, antisense sequence, siRNA, shRNA, probe or primer.

In another aspect, the invention relates to a vector comprising a polynucleotide of the invention or to a vector having DNA regulatory sequences functional in cells capable of enabling endogenous gene activation of a SIVA3 polypeptide and a host cell such as a eukaryotic cell selected from a mammalian (e.g. HeLa, 293 T HEK and CHO cells), insect, and yeast cell comprising such a vector.

In another further aspect, the invention provides a method of producing a SIVA3 polypeptide, comprising growing a host cell of the invention, and isolating the SIVA3 polypeptide produced. Also, a method of producing a SIVA3 polypeptide may comprise the generation of a transgenic animal and isolating the protein produced from the body fluids of the animal.

In another further aspect, the invention provides a SIVA3 polypeptide or a salt thereof encoded by the polynucleotide of the invention; having at least 20%, or 50%, 80%, 90% and 95% identity to the polypeptide comprising the amino acid sequence from amino acids 40 to 107 of SEQ ID NO: 1; or encoded by the nucleotide sequence set forth in SEQ ID NO: 2.

In still another further aspect, the invention provides a polyclonal or monoclonal antibody, chimeric antibody, fully humanized antibody, anti-anti-Id antibody or fragment thereof prepared using a SIVA3 polypeptide and capable of binding the polypeptide spanning amino acid 40 to 107 of SEQ ID NO:1.

It is one object of the invention to provide the use of a SIVA3 polypeptide of the invention or salt thereof; a polynucleotide sequence of the invention; a vector according of the invention; a host cell of the invention; and/or an antibody according of the invention, in the manufacture of a medicament for treating a disease, disorder or condition selected from developmental disorders; cell proliferative disorders such as neoplastic disorders, like melanoma, sarcoma, renal tumour, colon tumour; genetic disorders; nervous system disorders; metabolic disorders; infections and other pathological conditions; immune disorders such as osteoarthritis, autoimmune disease, autoimmune myocarditis I, rheumatoid arthritis, psoriasis, systemic multiple sclerosis, and lupus erythematosus; inflammatory disorders such as glomerulonephritis, allergy, rhinitis, HCV mediated chronic hepatitis, chronic gastritis e.g., type A gastritis, mixed connective tissue disease (MCTD), conjunctivitis, uveitis, diabetes, digestive system inflammation, autoimmune uveoretinitis, multiple sclerosis with primary oligodendrogliopathy, inflammatory bowel disease such as Crohn's disease and ulcerative colitis, myasthenia gravis, pancreatitis, sepsis, endotoxic shock, cachexia, myalgia, ankylosing spondylitis, asthma, airway inflammation; wound healing; dermatological disease; ageing; and infections, including plasmodium, bacterial infection and viral infection.

In one embodiment of the invention the use is for a disease, disorder, or condition characterized by increased host immune, inflammatory response and/or cell proliferation due to inappropriate NIK-mediated activity or NIK-mediated NF-κB activity in cells.

In another embodiment of the invention, the use is for a disease, disorder, or condition characterized by decreased host immune response and/or cell proliferation due to inappropriate NIK-mediated activity or NIK-mediated NF-κB activity in cells.

It is another object of the invention to provide the use of a SIVA3 polypeptide of the invention or salt thereof; a polynucleotide sequence of the invention; a vector of the invention; a host cell of the invention; and/or an antibody of the invention in the development of a method for detection of a SIVA3 polypeptide expression in a biological sample; a method for screening agonists and antagonists of SIVA3; a method of diagnosis of a disease, a method to follow up a therapy and/or a method for identiflying a disease, disorder or condition associated with the levels of SIVA3.

In one embodiment of the invention the method is for screening agonists and antagonists of SIVA3 that bind SIVA3 from a sample selected from body fluids, cell extracts and DNA expression libraries, comprising immunoprecipitating SIVA3 with an antibody of the invention and identifying the protein co-immunoprecipitated or using SIVA3 as the prey or the bait in the yeast two-hybrid procedure and clone the SIVA3 binding protein.

In another embodiment of the invention, the method is for the diagnosis of a proliferative disorder or an immune disorder in a subject comprising (a) obtaining a biological sample from the subject; and (b) detecting an altered level of SIVA3 in the sample compared to the level in a healthy subject, wherein said altered level is diagnostic of a proliferative disorder or an immune disorder in the subject.

In another further embodiment of the invention, the method is for the follow up of a therapy for a proliferative disorder or an immune disorder in a patient comprising (a) obtaining a biological sample from the patient before and after taking a therapy; and (b) detecting level of SIVA3 in the samples of the patient before or after taking the therapy and (c) comparing the level of SIVA3 in the patient before and after taking the therapy, wherein a change in the level of SIVA3 after taking the therapy is indicative of the efficiency of the therapy in the patient.

The invention also provides a pharmaceutical composition comprising a pharmaceutical acceptable carrier and a SIVA3 polypeptide of the invention or salt thereof; polynucleotide of the invention; a vector of the invention; a host cell of the invention; and/or an antibody of the invention.

It is also provided by the invention a method of screening for a polypeptide or a small molecule agonistic or antagonistic to SIVA3, comprising screening and selecting a molecule able to inhibit SIVA3-mediated NIK degradation; to inhibit NIK mediated NF-κB activation; and to inhibit interaction of SIVA3 polypeptide with cellular inhibitor of apoptosis protein 1 (cIAP1), or a TNF-receptor associated adaptor protein 2 (TRAF2).

Also, it provided by the invention a method of gene therapy for treatment of an immune disease or cancer comprising inducing the expression of a SIVA3 polypeptide or at a desired site in a human patient in need.

BRIEF DESCRIPTION OF THE FIGURES

FIG. 2 shows the nucleotide sequence of SIVA3 (SEQ ID NO: 2).

FIG. 3 shows the amino acid sequence of SIVA3 (SEQ ID NO: 1).

DETAILED DESCRIPTION OF THE INVENTION

Figures 1A, 1B:
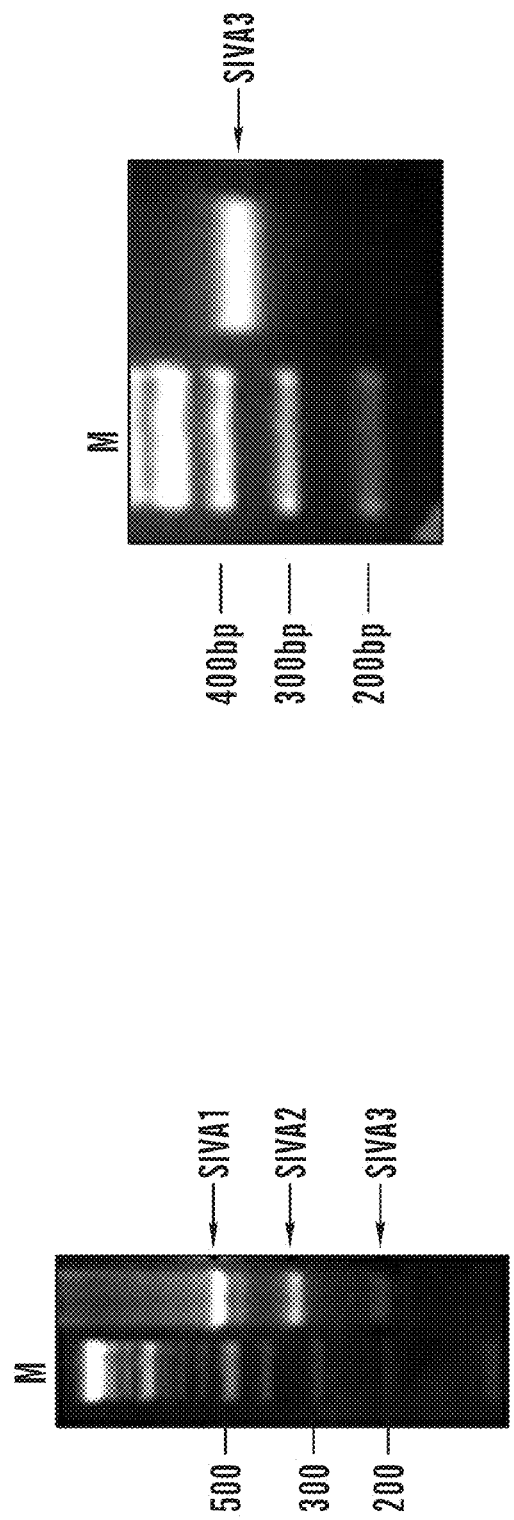
FIGS. 1A-1B shows that an additional isoform of SIVA (SIVA3) is expressed in peripheral blood mononuclear cells (PBMCs). (A) Employing the Reverse Transcript-Polymerase Chain Reaction (RT-PCR) expression of SIVA1, SIVA2, and SIVA3 was detected in resting PBMCs. M=molecular weight markers. (B) Full length SIVA3 amplified from PBMC.

The findings according to the invention show that a new splice variant of SIVA, named herein "SIVA3", is expressed in mononuclear cells. SIVA3, unlike the SIVA2 isoform, does not bind to NF-κB-inducing kinase (NIK) but, similar to SIVA2, it down-regulates NIK levels in cells; and is capable of binding cellular inhibitor of apoptosis protein 1 (CAIP1) and TNF-receptor associated adaptor protein 2 (TRAF2).

The present invention relates, in one aspect, to a SIVA3 polypeptide which is capable of modulating the intracellular level of NIK, especially, where NIK is involved in modulation or mediation of NF-κB induction such as in inflammation and cell survival pathways. Thus, the present invention relates to SIVA3, or to a SIVA3 mutein, isoform, fused protein, functional derivative, active fractions, fragment, circularly permutated derivative and salt. SIVA3 of sequence set forth in SEQ ID NO: 1, a mutein, isoform, fused protein, functional derivative, active fraction, fragment, and circularly permutated derivative thereof are collectively named herein "SIVA3 polypeptide". A SIVA3 polypeptide has at least part of the amino acid sequence spanning amino acid sequence 40 to 107 of SEQ ID NO: 1 or the sequence in FIG. 3. In one embodiment of the invention, SIVA3 polypeptide has at least 20%, or 50%, 80%, 90% and 95% identity to the polypeptide comprising the amino acid sequence from amino acids 40 to 107 of SEQ ID NO: 1. In another embodiment of the invention, SIVA3 polypeptide is encoded by whole or part of the nucleotide sequence set forth in SEQ ID NO: 2 (or in FIG. 2). In another further embodiment of the invention, SIVA3 polypeptide is encoded by a nucleotide sequence comprising nucleotides form 119 to 324 of SEQ ID NO: 2.

In addition to the use of a SIVA3 polypeptide or salt thereof, the invention relates to the use of a nucleic acid sequence encoding said polypeptide; a vector comprising said nucleic acid sequence; a host cell comprising said nucleic acid sequence or vector; a compound that can be effective to alter said polypeptide level in a tissue; and/or an antibody that recognizes and binds specifically to SIVA3 in diagnosis; treatment; follow up of therapy; and/or in screening methods for identification of agonists or antagonists of SIVA3.

The SIVA3 polypeptide which comprises its salts; functional derivatives; isoforms; active fractions; circularly permutated derivative; precursors and fragments as well as its muteins, i.e. other proteins or polypeptides wherein one or more amino acids of the structure were eliminated or substituted by other amino acids or one or more amino acids were added to that sequence in order to obtain polypeptides or proteins; should have substantially the same activity of the polypeptide comprising the amino acid sequence of SEQ ID NO: 1. Such polypeptide comprises also the corresponding "fusion proteins" i.e. polypeptides comprising the amino acid sequence of SEQ ID NO: 1 or a mutation thereof fused with another protein, for example, an immunoglobulin and having a longer lasting half-life in body fluids.

It should also be understood that the SIVA3 polypeptide according to the invention comprises a polypeptide encoded by a polynucleotide of the invention as defined below.

An example of the activity of SIVA3 set forth in SEQ ID NO: 1 includes, but is not limited to; down-regulation of NIK levels in a cell or tissue; down-regulation of NIK mediated NF-κB activation in a cell or tissue; binding cIAP1 and binding TRAF2. Thus the SIVA3 polypeptide of the invention will have at least one of these activities of SIVA3 set forth in SEQ ID NO: 1.

The term "salts" herein refers to both salts of carboxyl groups and to acid addition salts of amino groups of the polypeptide of the invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Of course, any such salts must have substantially similar activity to the SIVA3.

As used herein, the term "fragment" refers to a part or fraction of the polypeptide molecule, provided that the shorter peptide retains the desired biological activity of SIVA3. Fragments may readily be prepared by removing amino acids from either end of the polypeptide and testing the biological activity of the resulting fragment for example: binding to cIAP1, binding to TRAF2, induction of NIK degradation, and/or inhibition of NIK-mediated NFκB activation in cells. Proteases that remove one amino acid at a time from either the N-terminal or the C-terminal of a polypeptide are known in the art, and fragments that retain the desired biological activity can be obtaining as a matter of routine experimentation by employing such proteases.

As "active fractions" of the protein the present invention refers to any fragment or precursor of the polypeptidic chain of the compound itself, alone or in combination with related molecules or residues bound to it, for example residues of sugars or phosphates, or aggregates of the polypeptide molecule when such fragments or precursors show the same activity of SIVA3 as medicament. "Precursors" are compounds which can be converted into the SIVA3 in the human or animal body.

The definition "functional derivatives" as herein used refers to derivatives which can be prepared from the functional groups present on the lateral chains of the amino acid moieties or on the terminal N- or C-groups according to known methods and are comprised in the invention when they are pharmaceutically acceptable i.e. when they do not destroy the protein activity or do not impart toxicity to the pharmaceutical compositions containing them. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups. SIVA3 may be conjugated to polymers in order to improve the properties of the protein, such as the stability, half-life, bioavailability, tolerance by the human body, or immunogenicity. Therefore, one embodiment of the invention relates to a functional derivative of SIVA3 comprising at least one moiety attached to one or more functional groups, which occur as one or more side chains on the amino acid residues. One embodiment of the invention relates to SIVA3 polypeptide linked to Polyethlyenglycol (PEG). PEGylation may be carried out by known methods, such as the ones described in WO 92/13095, for example.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

As used herein the term "muteins" refers to analogs of SIVA3. The present invention also concerns analogs of the above SIVA3 protein of the invention, which analogs retain essentially the same biological activity of the SIVA3 protein having essentially only the naturally occurring sequences of SIVA3. Such "analogs" may be ones in which up to about 30 amino acid residues may be deleted, added or substituted by others in the SIVA3 protein, such that modifications of this kind do not substantially change the biological activity of the protein analog with respect to the protein itself. Thus, one or more of the amino acid residues of the naturally occurring components of SIVA3 are replaced by different amino acid residues, or are deleted, or one or more amino acid residues are added to the original sequence of SIVA3, without changing considerably the activity of the resulting products as compared with the original SIVA3. These muteins are prepared by known synthesis and/or by site-directed mutagenesis techniques, or any other known technique suitable therefore.

Any such mutein preferably has a sequence of amino acids sufficiently duplicative of that of the basic SIVA3 such as to have substantially similar activity thereto. Thus, it can be determined whether any given mutein has substantially the same activity as the basic SIVA3 of the invention by means of routine experimentation comprising subjecting such an analog to the biological activity tests set forth in Examples below e.g. monitoring binding to cIAP1, binding to TRAF2, induction of NIK degradation, and/or inhibition of NIK-mediated NFκB activation in cells.

Muteins of the SIVA3 protein which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., Principles of Protein Structure, Springer-Verlag, New York, 1978; and Creighton, T. E., Proteins: Structure and Molecular Properties, W.H. Freeman & Co., San Francisco, 1983, which are hereby incorporated by reference. For a presentation of nucleotide sequence substitutions, such as codon preferences, see . See Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

Preferred changes for muteins in accordance with the present invention are what are known as "conservative" substitutions. Conservative amino acid substitutions of those in the SIVA3 protein having essentially the naturally—occurring SIVA3 sequences, may include synonymous amino acids within a group which have sufficiently similar physicochemical properties that substitution between members of the group will preserve the biological function of the molecule, Grantham, Science, Vol. 185, pp. 862-864 (1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues, Anfinsen, "Principles That Govern The Folding of Protein Chains", Science, Vol. 181, pp. 223-230 (1973). Analogs produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser. Ala, Gly, His, Gln, Thr |
| Ala | Gly, Thr, Pro, Ala |
| Val | Met, Tyr, Phe, Ile, Leu, Val |
| Gly | Ala, Thr, Pro, Ser. Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonimous Amino Acids

| Amino Acid | Synonymous Group |
|---|---|
| Ser | Ser |
| Arg | His, Lys, Arg |
| Leu | Ile, Phe, Met, Leu |
| Pro | Ala, Pro |
| Thr | Thr |
| Ala | Pro, Ala |
| Val | Met, Ile, Val |
| Gly | Gly |
| Ile | Ile, Met, Phe, Val, Leu |
| Phe | Met, Tyr, Ile, Leu, Phe |
| Tyr | Phe, Tyr |
| Cys | Ser, Cys |
| His | Arg, Gln, His |
| Gln | Glu, His, Gln |
| Asn | Asp, Asn |
| Lys | Arg, Lys |
| Asp | Asn, Asp |
| Glu | Gln, Glu |
| Met | Phe, Ile, Val, Leu, Met |
| Trp | Trp |

TABLE III

Most Preferred Groups of Synonymous Amino Acids

| Amino Acid | Synonymous Group |
|---|---|
| Ser | Ser |
| Arg | Arg |
| Leu | Ile, Met, Leu |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Ser, Cys |
| His | His |
| Gln | Gln |
| Asn | Asn |
| Lys | Lys |
| Asp | Asp |
| Glu | Glu |
| Met | Ile, Leu, Met |
| Trp | Trp |

Examples of production of amino acid substitutions in proteins which can be used for obtaining muteins of SIVA3 include any known method steps, such as presented in U.S. Pat. RE 33,653, U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Straw et al).

In another preferred embodiment of the present invention, any mutein of the SIVA3 protein for use in the present invention has an amino acid sequence essentially corresponding to that of the above noted SIVA3 protein of the invention. The term "essentially corresponding to" is intended to comprehend muteins with minor changes to the sequence of the basic SIVA3 protein which does not affect the basic characteristics thereof, particularly insofar as its ability to SIVA3 is concerned. The type of changes which are generally considered to fall within the "essentially corresponding to" language are those which would result from conventional mutagenesis techniques of the DNA encoding the SIVA3 protein of the invention, resulting in a few minor modifications, and screening for the desired activity in the manner discussed above.

In one embodiment of the invention, any such mutein has at least 40% identity with the sequence of SIVA3 set forth in SEQ ID NO:1, more preferably, it has at least 50%, at least 60%, at least 70%, at least 80% or, most preferably, at least 90% identity thereto. In a further embodiment of the invention, any such mutein has at least 20% identity with the sequence of SIVA3 from amino acids 40 to 107, more preferably, it has 40%, at least 50%, at least 60%, at least 70%, at least 80% or, most preferably, at least 90% identity with the sequence of SIVA3 from amino acids 40 to 107.

The present invention also encompasses SIVA3 isoforms or splice variants except for SIVA1 and SIVA2. Different forms of a protein may be produced from different but related genes, or may arise from the same gene by alternative splicing. Also, isoforms are formed by single nucleotide polymorphisms, small genetic differences between alleles of the same gene. A protein isoform is a version of a protein with only small differences to another isoform of the same protein. In one embodiment of the invention, a SIVA3isoform is one having at least 50% and 80% amino acid identity, a more preferred isoform is one having at least 90% identity and a most preferred variant is one having at least 95% identity to the polypeptide comprising the amino acid sequence of SEQ ID NO: 1. In a further embodiment of the invention, SIVA3isoform is one having at least 20%, or 50%, 80%, 90% and 95% identity to the amino acid sequence from amino acids 40 to 107 of SEQ ID NO: 1.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

The term "sequence identity" as used herein means that the amino acid sequences are compared by alignment according to Hanks and Quinn (1991) with a refinement of low homology regions using the Clustal-X program, which is the Windows interface for the ClustalW multiple sequence alignment program (Thompson et al., 1994). The Clustal-X program is available over the internet at ftp://ftp-igbmc.u-strasbg.fr/pub/clustalx/. Of course, it should be understood that if this link becomes inactive, those of ordinary skill in the art can find versions of this program at other links using standard internet search techniques without undue experimentation. Unless otherwise specified, the most recent version of any program referred herein, as of the effective filing date of the present application, is the one which is used in order to practice the present invention.

If the above method for determining "sequence identity" is considered to be nonenabled for any reason, then one may determine sequence identity by the following technique. The sequences are aligned using Version 9 of the Genetic Computing Group's GDAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Muteins in accordance with the present invention include those encoded by a nucleic acid, such as DNA or RNA, which hybridizes to DNA or RNA under stringent conditions and which encodes a SIVA3 protein in accordance with the present invention, comprising essentially all of the naturally-occurring sequences encoding SIVA3. For example, such a hybridizing DNA or RNA may be one encoding the same protein of the invention having, for example, the sequence set forth in FIG. 2. and SEQ ID NO:1, but which nucleotide differs in its nucleotide sequence from the naturally-derived nucleotide sequence by virtue of the degeneracy of the genetic code, i.e., a somewhat different nucleic acid sequence may still code for the same amino acid sequence, due to this degeneracy.

The term "hybridization" as used herein shall include any process by which a strand of nucleic acid joins with complementary strand through a base pairing (Coombs J, 1994, Dictionary of Biotechnology, Stockton Press, New York N.Y.). "Amplification" is defined as the production of additional copies of a nucleic acid sequence and is generally carried out using polymerase chain reaction technologies well known in the art (Dieffenbach and Dveksler, 1995, PCR Primer, a Laboratory Manual, Cold Spring Harbor Press, Plainview N.Y.).

"Stringency" typically occurs in a range from about Tm-5° C. (5° C. below the melting temperature of the probe) to about 20° C. to 25° C. below Tm.

The term "stringent conditions" refers to hybridization and subsequent washing conditions which those of ordinary skill in the art conventionally refer to as "stringent". See Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

As used herein, stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA-DNA hybrid:

$$Tm=81.5 \, C+16.6 \, (\text{Log } M)+0.41 \, (\% \, GC)-0.61 \, (\% \, \text{form})-500/L$$

where M is the molarity of monovalent cations, % GC is the percentage of G and C nucleotides in the DNA, % form is the percentage of formamide in the hybridization solution, and L is the length of the hybrid in base pairs. For each 1 C that the Tm is reduced from that calculated for a 100% identity hybrid, the amount of mismatch permitted is increased by about 1%. Thus, if the Tm used for any given hybridization experiment at the specified salt and formamide concentrations is 10 C below the Tm calculated for a 100% hybrid according to the equation of Meinkoth, hybridization will occur even if there is up to about 10% mismatch.

As used herein, "highly stringent conditions" are those which provide a Tm which is not more than 10 C below the Tm that would exist for a perfect duplex with the target sequence, either as calculated by the above formula or as actually measured. "Moderately stringent conditions" are those which provide a Tm which is not more than 20 C below the Tm that would exist for a perfect duplex with the target sequence, either as calculated by the above formula or as actually measured. Without limitation, examples of highly stringent (5-10 C below the calculated or measured Tm of the hybrid) and moderately stringent (15-20 C below the calculated or measured Tm of the hybrid) conditions use a wash solution of 2×SSC (standard saline citrate) and 0.5% SDS (sodium dodecyl sulfate) at the appropriate temperature below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6× SSPE (standard saline-phosphate-EDTA)), 5× Denhardt's reagent, 0.5% SDS, 100 µg/ml denatured, fragmented salmon sperm DNA at a temperature approximately 20 to 25 C below the Tm. If mixed probes are used, it is preferable to use tetramethyl ammonium chloride (TMAC) instead of SSC (Ausubel, 1987, 1999).

The DNA sequences of SIVA3 (SEQ ID NO 2) and the corresponding predicted amino acid sequences (SEQ ID NO:1) were established according to the invention and are disclosed in FIGS. 2 and 3, respectively. It was found that SIVA3 splice variant is encoded by exons 1 and 4, and has very little homology to SIVA 1 or SIVA 2. In fact, SIVA3 is about 35% (39 amino acids of 110) identical to SIVA2 and less 22% (39 of 175 amino acids) to SIVA1.

Thus the invention relates to purified or isolated polynucleotide such as: (a) a polynucleotide encoding a SIVA3 polypeptide selected from a polypeptide comprising the amino acid sequence of SEQ ID NO: 1, a mutein, isoform, fused protein, functional derivative, fragment, active fraction, circularly permutated derivative thereof; (b) a polynucleotide comprising a sequence capable of hybridizing under moderately stringent conditions to a polynucleotide sequence spanning nucleotides 119 to 324 of SEQ ID NO: 2 or to a fragment thereof (c) a polynucleotide comprising a fragment spanning at least 10, 11-29, 30-50, and 50-199 consecutive nucleotides, and a fragment of 200-205 consecutive nucleotides from nucleotide residue 119 to 324 of SEQ ID NO: 2.

The invention also provides a purified nucleic acid molecule or polynucleotide which encodes a polypeptide of the invention. The invention provides also a purified nucleic acid molecule or polynucleotide which hybridizes under high stringency conditions with a nucleic acid molecule of the invention; encoding a polypeptide of the invention; which hybridizes under medium stringency to a polypeptide encoding amino acid residues 40-107 of SEQ ID NO: 1; or which hybridizes under medium stringency to a polynucleotide fragment from nucleotide residue 119 to 324 of SEQ ID NO: 2; or a clone of deposit number CNCM 1-3880 having the sequence of SEQ ID NO: 2.

The term "nucleic acid molecule" or "polynucleotide" as used herein refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The polynucleotides of the invention include also polynucleotides that comprise degenerate codons and/or which hybridize under highly stringent conditions to the complementary sequences of the sequences set forth hereinabove.

Polynucleotides of SIVA3 may be used as probes and/or primers to detect the expression level of a SIVA3 polypeptide in a sample, for example by Northern blot analysis or PCR. SIVA3 polynucleotide of at least 10, preferably 19-29, consecutive nucleotides, can be used as a primer (As shown in one example summarized in FIG. 1) and a fragment spanning 200-2500 consecutive nucleotides can be used as a probe. In one embodiment, the invention provides a fragment spanning at least 10, preferably 19-29, and 30-50 consecutive nucleotides, and a fragment spanning 50-200 consecutive nucleotides fragment from nucleotide residue 119 to 324 of SEQ ID NO: 2.

The following primers can be used to detect SIVA3 expression by PCR CGCGGATCCACCATGCCCAAGCG-GAGCTGCCCC (SEQ ID NO: 3), and reverse: CCGCTC-GAGGCCAGCCTCAGGTCTCGAACATGG (SEQ ID NO: 4) at the original stop codon of SIVA1 and SIVA2. However, for monitoring exclusively the full length SIVA3 expression the following primers can be used, forward: CGCGGATC-CACCATGCCCAAGCGGAGCTGCCCC (SEQ ID NO: 5) and Reverse: CCGCTCGAGAGAGGTTTATTCATTCTGT-CATTAGG (SEQ ID NO: 6), at the first stop codon arising after the frame shift, after the original stop codon).

Also, polynucleotide of the invention may be used as small interference RNA (siRNA) to silence or inhibit SIVA3 in a cell. Thus, the invention provides a siRNA comprising between 15 and 30 consecutive nucleotides of a nucleic acid sequence that is identical on the RNA level to a sequence of SEQ ID NO: 2. In one embodiment, the invention provides a siRNA comprising between 15 and 30 consecutive nucleotides of a nucleic acid sequence that is identical on the RNA level to a sequence from nucleotide residue 119 to 324 of SEQ ID NO: 2. It should be noted that the invention is not intended to include and does not include any fragment/siRNA that contains a sequence that is present as a continuous stretch of nucleotides in the nucleic acid sequence of SIVA1 or SIVA2.

siRNA is widely used for post-transcriptional silencing of specific mRNA targets. siRNA consists of double stranded RNA, of 15 and 30 bp long and typically of 9-21 bp long, with two nucleotides overhanging at each 3' end. Alternatively, 27-mer blunt-ended nucleotides may be used. For example, a specific siRNA can be used for post-transcriptional silencing of specific mRNA targets (Dorsett and Tuschl 2004). Target specificity in RNAi is achieved through RNA-RNA sequence recognition and base pairing. The siRNA consists of double stranded RNA, typically of 19-21 base pair long, with two nucleotides overhanging at each 3' end. For maximal stability, two 2' deoxynucleotides are used as 3' overhangs. Alternatively, 27-mer blunt-ended nucleotides may be used, as these have shown improved efficiency in gene silencing (Kim, Behlke et al. Nat Biotechnol. 2005 February; 23(2):222-6. Epub 2004 Dec. 26.). Transport of siRNA into cells may be enhanced by encapsulation into liposomes or by covalent coupling to highly lipophilic agents. Soutschek et al (2004).

Another example of an inhibitor of expression of a SIVA3 polypeptide is a specific short hairpin RNA (shRNA). Designing and cloning strategies for constructing shRNA expression vectors are known in the art (McIntyre and Gregory et al BMC Biotechnology 2006, 6:1).

Given the known mRNA sequence of a gene, ribozymes may be designed, which are RNA molecule that specifically bind and cleave said mRNA sequence (see e.g., Chen et al. Ann N Y Acad Sci. 1992 Oct. 28; 660:271-3; Nucleic Acids Res. 1992 Sep. 11; 20(17):4581-9, Zhao and Pick, Nature. 1993 Sep. 30; 365(6445):448-51., Shore et al., Oncogene. 1993 November; 8(11):3183-8, Joseph and Burke, J Biol Chem. 1993 Nov. 25; 268(33):24515-8, Shimayama et al., Nucleic Acids Symp Ser. 1993; (29):177-8).

It is also provided according to the invention a vector that comprises a polynucleotide of the invention and a host cell harbouring said vector.

In one embodiment, the invention provides a polynucleotide of SIVA3 operatively linked to one or more other polynucleotides such as transcription and translation regulatory elements. Such a polypeptide can be contained in a vector, which can be an expression vector, and the nucleic acid molecule or the vector can be contained in a host cell. Examples of vectors include, but are not limited to, a cloning vector, an expression vector, a plasmid vector, and a viral vector. Generally, besides of the polynucleotide of the invention, the vector can contain a selectable marker, a transcription regulatory element such as a promoter or polyadenylation signal sequence, or a translation regulatory element such as a ribosome binding site. A promoter sequence can provide tissue-specific expression of a polynucleotide operatively linked thereto.

The vector generally contains elements required for replication in a prokaryotic or eukaryotic host system, or both, as desired. Such vectors include plasmid vectors and viral vectors such as bacteriophage, baculovirus and viral vectors developed for use in particular host systems, particularly mammalian systems and include, for example, retroviral vectors, other lentivirus vectors such as those based on the human immunodeficiency virus (HIV), adenovirus vectors, adeno-associated virus vectors, herpes virus vectors, vaccinia virus vectors, and the like. These virus vectors are well known and commercially available.

An expression vector can be transfected into a recombinant host cell for expression of a SIVA3 polypeptide. The host cell can be prokaryotic, e.g., bacterial cells, or eukaryotic, e.g., yeast or mammalian cells. The host cells can be selected, for example, for high levels of expression in order to obtain a large amount of isolated protein. A host cell can be maintained in cell culture, or can be a cell in vivo in an organism.

The invention provides also a method of producing a SIVA3 polypeptide.

A polypeptide of the invention can be produced by culturing host cells containing a vector comprising a polynucleotide of the invention under suitable conditions to express said polypeptide, and optionally isolating the polypeptide from the culture medium.

Furthermore, the invention provides a host cell selected from prokaryotic or eukaryotic cells, such as a mammalian, insect, and yeast cells. In one embodiment of the invention the cells are HeLa, 293 THEK or CHO cells, comprising an expression vector encoding a polypeptide of the invention in a method of producing a polypeptide of the invention. Alternatively, the invention provides a method of producing a polypeptide of the invention comprising the generation of a transgenic animal and isolating the protein produced from the body fluids of the animal.

A SIVA3 polypeptide, can be produced either in bacterial or eukaryotic host cells transfected, transformed or infected with vectors encoding such polypeptide, or in transgenic animals. When using transgenic animals, it is particularly advantageous to produce heterologous polypeptides in their milk.

Expression of a SIVA3 polypeptide in a mammalian cell may be carried out by inserting the DNA encoding the polypeptide into a vector comprising a promoter, optionally an intron sequence and splicing donor/acceptor signals, and further optionally comprising a termination sequence and signal peptide for secretion, by well-known techniques (for example, as described in Current Protocols in Molecular Biology, chapter 16).

Expression of a SIVA3 polypeptide in a mammalian cell may be carried out by inducing increase in expression of the endogenous gene which encodes SIVA3 polypeptide. Altering expression of endogenous SIVA3 can be also employed to treat a disease disorder or condition. The invention encompasses compounds that can be effective to alter the levels of endogenous polypeptide of the invention or that can regulate the activity of the endogenous polypeptide. If desired, a compound of the invention may either increase or decrease the level of expression of the gene or the activity of the endogenous polypeptide. Such compound can be a vector for inducing the endogenous production of a SIVA3 polypeptide in a cell which expresses amounts of the polypeptide which are not sufficient. The vector may comprise regulatory sequences functional in the cells desired to express the SIVA3 polypeptide. Such regulatory sequences may be promoters or enhancers, for example. The regulatory sequence may then be introduced into the right locus of the genome by homologous recombination, thus operably linking the regulatory sequence with the gene, the expression of which is required to be induced or enhanced. The technology is usually referred to as "Endogenous Gene Activation" (EGA), and it is described e.g. in WO 91/09955.

It will be understood by the person skilled in the art that it is also possible to shut down SIVA3 polypeptide expression directly, in situations in which the endogenous SIVA3 polypeptide is over-expressed and results in excessive amounts of the polypeptide in a cell. To do that, a negative regulation element, like e.g. a silencing element, may be introduced into the gene locus of SIVA3, thus leading to down-regulation or prevention of SIVA3 expression. The person skilled in the art will understand that such down-regulation or silencing of SIVA3 expression has the same effect as the use of an SIVA antagonist in order to prevent and/or treat disease.

The invention also provides methods for screening agonists and antagonists of SIVA3.

Identification of the function of SIVA3 polypeptide paves the way for the design of screening methods for the identification of compounds that can be used in the treatment and/or diagnosis of disease. It was found according to the invention that increasing the level of SIVA3 in HeLa cells induces degradation of NIK in these cells. Thus, it was found according to the invention that SIVA3 is capable of regulating the levels of NIK and the activity of NFκB induced via the alternative pathway since degradation of NIK mediated by SIVA3 was followed by changes in cellular levels of p100/p52. It was found according to the invention that despite of the difference in sequence between SIVA3 and SIVA2 and although SIVA3 unlike SIVA2 does not bind NIK, SIVA3 can induce NIK degradation like SIVA2. Thus, the endogenous splice variant or isoform SIVA3 does not bind to NIK, down-regulates NIK levels in cells, affects NIK mediated NFικB activation, is capable of binding, and may regulate, cIAP1 and TRAF2. Therefore agonists and antagonist of SIVA3 which bind specifically to SIVA3 (and not to SIVA2 or SIVA1) and can regulate the function of a SIVA3 polypeptide of the invention, said agonists and antagonists named herein "SIVA3 modulating compounds", can be identified. The SIVA3 modulating compounds can be proteins such as enzymes, antibodies, natural or modified substrates, receptors, small organic molecules which may be organic molecules of up to 2500 Daltons, preferably 850 Daltons or less, peptidomimetics, inorganic molecules, structural or functional mimetics of the abovementioned. A SIVA3 modulating compound can be identified that can alter the expression of a natural gene which encodes a SIVA3 polypeptide or that can regulate the activity of a SIVA3 polypeptide.

SIVA3 modulating compounds capable of altering the expression and/or activity of SIVA3 may be identified using the above mentioned activities of SIVA3 in screening methods. For example, a screening method may comprise testing the effect of candidate compounds, for example, on SIVA3-mediated regulation of NIK levels in cells, SIVA3-mediated inhibition of NFκB activation, binding of SIVA3 to cIAP1 and binding of SIVA3 to TRAF2. Such screening methods are included as aspects of the present invention.

In one embodiment of the invention, the invention provides a method for screening a peptide or a small molecule agonistic or antagonistic to SIVA3, which comprises: (i) contacting SIVA3 and NIK in the presence or in the absence of a candidate agent, under conditions which allow degradation of NIK (ii) measuring the level of NIK and/or p100/p52 in the presence or in the absence of said candidate agent; and (iii) comparing the level of NIK and/or p100/p52 in the presence and in the absence of said candidate agent, wherein a change in the level of NIK and/or p100/p52 in the presence of said candidate agent is indicative that the candidate agent is capable of modulating the level of NIK and/or NIK mediated NFκB and can be used as agonist if increases degradation of NIK and/or inhibition degradation of P100 or antagonist if inhibits degradation of NIK mediated by SIVA3 and/or inhibition degradation of P100.

In a further embodiment, the screening assay is a cell based assay, and said contacting is carried out inside the cells. The cells can be recombinant cells expressing tagged 1-NIK expression vector and tagged 2-SIVA3 expression vector and the cellular levels of NIK and/or p100/p52 are assessed by western blotting using antibody specific antibody to Tag1 and/or antibody to p100 and/or p52 as exemplified below.

In one additional embodiment, the invention provides a method for screening a peptide or a small molecule agonistic or antagonistic to SIVA3, which comprises: (i) contacting SIVA3 with TRAF2 or CIAP1 in the presence or in the absence of a candidate agent, under conditions which allow binding of SIVA3 to TRAF2 or CIAP1 (ii) measuring the level of SIVA3-TRAF2 or SIVA3-CIAP1 complex in the presence or in the absence of said candidate agent; and (iii) comparing the level of SIVA3-TRAF2 or SIVA3-CIAP1 complex in the presence and in the absence of said candidate agent, wherein a change in the level of SIVA3-TRAF2 or SIVA3-CIAP1 complex in the presence of said candidate agent is indicative that the candidate agent is capable of modulating the level of SIVA3-TRAF2 or SIVA3-CIAP1 complex and is an agonist or antagonist of SIVA3.

In one embodiment, the SIVA3 agonist or antagonist compound can be derived from a sample selected from body fluids, cell extracts and DNA expression libraries. The agonist antagonist protein can be isolated by screening methods including, but not limited to, co-immunoprecipitation of SIVA3 polypeptide with a specific antibody as shown in the examples below; two-hybrid procedure which is a well known in the art (and is described in U.S. Pat. No. 7,189,535) using SIVA3 polypeptide as the prey or the bait; and by affinity chromatography using immobilized SIVA3 polypeptide.

The invention also provides a polyclonal or monoclonal antibody, chimeric antibody, fully humanized antibody, anti-anti-Id antibody or fragment thereof prepared using a SIVA3 polypeptide comprising the amino acid sequence of SEQ ID NO: 1, and especially sequences spanning amino acids from 40 to 107. This definition excludes antibodies capable of binding also SIVA1 and SIVA2.

"Fully humanized antibodies" are molecules containing both the variable and constant region of the human immunoglobulin. Fully humanized antibodies can be potentially used for therapeutic use, where repeated treatments are required for chronic and relapsing diseases such as autoimmune diseases. One method for the preparation of fully human antibodies consist of "humanization" of the mouse humoral immune system, i.e. production of mouse strains able to produce human Ig (Xenomice), by the introduction of human immunoglobulin (Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunization with antigen.

Fully humanized antibodies and methods for their production are known in the art (Mendez et al., Nature Genetics 15:146-156 (1997); Buggemann et al., Eur. J. Immunol. 21:1323-1326 (1991); Tomizuka et al., Proc. Natl. Acad. Sci. USA 97:722-727 (2000) Patent WO 98/24893.

Another type of antibody is an anti-idiotypic antibody. An anti-idiotypic (anti-Id) antibody is an antibody, which recognizes unique determinants generally associated with the antigen-binding site of an antibody. An Id antibody can be prepared by immunizing an animal of the same species and genetic type (e.g. mouse strain) as the source of the Mab to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb, which induced the anti-Id. Thus, by using antibodies to the idiotypic determinants of a mAb, it is possible to identify other clones expressing antibodies of identical specificity.

The term "antibody" is also meant to include both intact molecules as well as fragments thereof, such as, for example, Fab and F (ab') 2, which are capable of binding antigen. Fab and F (ab') 2 fragments lack the Fc fragment of intact antibody, clear more rapidly from the circulation, and may have less non-specific tissue binding than an intact antibody (Wahl et al., 1983).

It will be appreciated that Fab and F (ab') 2 and other fragments of the antibodies useful in the present invention may be used for the detection and quantitation of a SIVA3 polypeptide according to the methods disclosed herein for intact antibody molecules. Such fragments are typically produced by proteolytic cleavage, using enzymes such as papain (to produce Fab fragments) or pepsin (to produce F (ab') 2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody, which can also be recognized by that antibody. Epitopes or "antigenic determinants" usually consist of chemically active surface groupings of molecules such as amino acids or sugar side chains and have specific three-dimensional structural characteristics as well as specific charge characteristics.

The antibodies (or fragments thereof) useful in the present invention may be employed histologically, as in immunofluorescence or immunoelectron microscopy, for in situ detection of SIVA3. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of SIVA3 polypeptide, but also its distribution on the examined tissue. Using the present invention, those of ordinary skill will readily perceive that any of wide variety of histological methods (such as staining procedures) can be modified in order to achieve such in situ detection.

Such assay for determination of the level of the SIVA3 polypeptide of the present invention typically comprises incubating a biological sample, such as a biological fluid, a tissue extract from freshly harvested cells such as lymphocytes or leukocytes, or cells which have been incubated in tissue culture, in the presence of a detectably labeled antibody capable of identifying the SIVA3 polypeptide, and detecting the antibody by any of a number of techniques well known in the art.

"Biological fluid" or biological sample denotes any fluid derived from or containing cells, cell components or cell products. Biological fluids include, but are not limited to, cell culture supernatants, cell lysates, cleared cell lysates, cell extracts, tissue extracts, blood, plasma, serum, milk and fractions thereof.

The biological sample may be treated with a solid phase support or carrier such as nitrocellulose, or other solid support or carrier, which is capable of immobilizing cells, cell particles or soluble polypeptides. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of antibody, of the invention as noted above, may be determined according to well-known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety, which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods, which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescent labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as 152E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including un-reacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the un-reacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and un-complexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of un-reacted labeled antibody. The determination of labeled antibody associated with a solid support or carrier is then determined as in the "simultaneous" and "forward" assays.

The creation of immunoassays, such as RIA or ELISA, has been described in many articles, textbooks, and other publications. Reference is made to WO 97/03998, p. 48, line 4 to p. 52, line 27. Immunoassays of the invention may be if two general types: Firstly, immunoassays using immobilized SIVA3 polypeptide, or an equivalent peptide, may be used in the quantification of SIVA3. Secondly, immunoassays using immobilized antibodies directed against an epitope of a SIVA3 polypeptide may be used to quantify SIVA3 polypeptides.

Such assays may find use in diagnostics, as the level of SIVA3 and of other polypeptides involved in apoptotic and/or immunologic pathways may need to be evaluated in a number of diseases, disorders, or conditions where involvement of such pathways is a possibility.

The terms protein and polypeptide are interchangeable in the present specification.

The invention also provides the use of following agents of the invention such as a SIVA3 polypeptide or salt thereof; a polynucleotide sequence; a vector; a host cell according to the invention; and/or an antibody in a method for the diagnosis of a disease such as a proliferative disorder or an immune disorder in a subject comprising (a) obtaining a biological sample from the subject; and (b) detecting an altered level of SIVA3 in the sample compared to the level in a healthy subject, wherein said altered level is diagnostic of said disease.

A similar assay can be used to follow up the effectiveness of a specific therapy for a proliferative disorder or an immune disorder in a patient. Thus a SIVA3 polypeptide or salt thereof; a polynucleotide sequence; a vector; a host cell according to the invention; and/or an antibody can be used in a method for the follow up of a therapy for a proliferative disorder or an immune disorder in a patient comprising (a) obtaining a biological sample from the subject; and (b) detecting level of SIVA3 in the sample compared to the level in a healthy subject or of the patient before during or after taking said therapy, wherein said level is closer to the healthy subject or change to a more normal level in the patient after or during taking the therapy is indicative of the efficiency of the therapy in the patient The effect of SIVA3 on NIK has several consequences: Firstly, degradation of NIK activity. This is demonstrated herein in a cell based assay wherein overexpressed SIVA3 induces degradation of NIK. Secondly, inhibition of NFκB. This is demonstrated herein in a cell based assay wherein overexpressed SIVA3 reduces NFκB activation induced by overexpression of NIK. Consequently, SIVA3 polypeptide, antibody or a nucleic acid molecule, or a vector, SIVA3 modulating compound or a host cell of the invention are useful in modulating the activity of NIK and NFκB for example, in a disease, disorder, or condition characterized by inappropriate NIK-mediated activity or NIK-mediated NF-κB activity such as for example in developmental disorders, cell proliferative disorders and immune disorders. In one embodiment of the invention, the disease, disorder, or condition is characterized by increased host immune, inflammatory response and/or cell proliferation mediated by increased NIK and NFκB activity and thus a SIVA3 polypeptide or any other agonist may be used to treat said disease, disorder or condition. In another embodiment, the disease, disorder, or condition is characterized by decreased host immune response and/or cell proliferation mediated by decrease NIK and NFκB activity, thus silencing of SIVA3 polypeptide for example with a specific siRNA, shRNA, a ribozyme, antibody or any other antagonist can be used.

Thus, the SIVA3 polypeptide, antibody or a nucleic acid molecule, a SIVA3 modulating compound, a vector, or a host cell of the invention can be used in therapy (prevention or treatment) or diagnosis of situations associated with the level or activity of SIVA3. Such situations may include diseases disorders or conditions such as developmental disorders; cell proliferative disorders for example neoplastic disorders, like cancer, melanoma, sarcoma, renal tumour, colon tumour; genetic disorders; nervous system disorders; metabolic disorders; infections and other pathological conditions; immune disorders such as osteoarthritis, autoimmune disease, rheumatoid arthritis, psoriasis, systemic multiple sclerosis, and lupus erythematosus; inflammatory disorders such as glomerulonephritis, allergy, rhinitis, conjunctivitis, uveitis, digestive system inflammation, inflammatory bowel disease such as Crohn's disease and ulcerative colitis, myasthenia gravis, pancreatitis, sepsis, endotoxic shock, cachexia, myalgia, ankylosing spondylitis, asthma, airway inflammation; wound healing; dermatological disease; ageing; and infections, including plasmodium, bacterial infection and viral infection. Thus, SIVA3 polypeptide, or a nucleic acid molecule, or a vector, or a host cell, or a SIVA3 binding compound of the invention may be used in the manufacture of a medicament for the treatment of such situations.

In one embodiment of the invention, diseases, disorders or conditions associated with decreased SIVA3, increased NIK activity and/or NFκB activity such as malignancies, including both primary tumor and metastasis, may be treated by administering a polypeptide of the invention capable of downregulating/inhibiting the activity of NIK and/or NFκB activity.

In another embodiment of the invention, diseases, disorders or conditions associated with decreased SIVA3, increased NIK activity and/or NFκB activity such inflammatory diseases, disorders or conditions may be treated by administering a polypeptide of the invention capable of downregulating/inhibiting the activity of NIK and/or NFkB activity.

The invention provides the use of SIVA3 polypeptide, antibody or a nucleic acid molecule, a SIVA3 modulating compound, a vector, or a host cell of the invention of the invention and other compounds capable of altering the activity or level of SIVA3 to change SIVA3 level or activity in cells to modulate/mediate intracellular effects on the inflammation, cell death or cell survival pathways in which SIVA3 is involved directly, or indirectly via other modulators/mediators of these pathways. The use comprises treating said cells with one or more of the following molecules: a SIVA3 polypeptide, SIVA3 specific antibody or a nucleic acid molecule, a SIVA3 modulating compound, a SIVA3 encoding vector, and compounds capable of altering the activity or level of SIVA3, wherein said treating of said cells comprises introducing into said cells said one or more molecules. In one embodiment of the invention, a SIVA3 polynucleotide of the invention is carried in a suitable vector which is capable of effecting the insertion of said polynucleotide into said host cells in a way that said sequence is expressed in said cells. The vector can be a virus vector carrying a sequence encoding a viral surface protein (ligand) that is capable of binding to a specific cell surface receptor on the surface of said cells to be treated and a second sequence encoding a polypeptide of the invention that when expressed in said cells is capable of altering the activity of SIVA3.The treatment is effected by infecting said cells with said vector.

Altering SIVA3 levels or activity in cells using SIVA3 polypeptide, antibody or a nucleic acid molecule, a SIVA3 modulating compound, a vector, or a host cell of the invention can comprise treating said cells with a SIVA3 polypeptide, SIVA3 specific antibody or a nucleic acid molecule, a SIVA3 modulating compound, a SIVA3 encoding vector, a cell expressing a SIVA3 polypeptide, and compounds capable of altering the activity or level of SIVA3, said treating being carried out by application of a suitable compound where they are exposed on the extracellular surface in said cells, and said composition is formulated for extracellular application, or being affected by intracellular way in said cells and said composition is formulated for intracellular application.

A SIVA3 polypeptide, SIVA3 specific antibody or a nucleic acid molecule, a SIVA3 modulating compound, and a SIVA3 encoding vector can be used for modulating processes modulated/mediated in cells by SIVA3 directly or indirectly. The use comprises treating said cells with SIVA3 polypeptide, antibody or a nucleic acid molecule, a SIVA3 modulating compound, a vector, or a host cell of the invention and other compounds capable of altering the activity or level of SIVA3 wherein said treating of said cells comprises introducing into said cells SIVA3 polypeptide, antibody or a nucleic acid molecule, a SIVA3 modulating compound, a vector, or a host cell of the invention and other compounds capable of altering the activity or level of SIVA3. In one embodiment the modulating processes that are mediated/modulated by SIVA3 includes NIK activity and NF-κB activity in cells. Non limiting examples of cells that can be treated are tumor cells, HIV-infected cells or other diseased cells such as mononuclear diseased cells. In one embodiment of the invention, said tumor or HIV-infected cells or other diseased cells are infected with a recombinant animal virus vector carrying a sequence encoding a viral surface protein capable of binding to a specific tumor cell surface receptor or HIV-infected cell surface receptor or receptor carried by other diseased cells such as a diseased mononuclear cell and a sequence encoding a SIVA3 polypeptide, that when expressed in said tumor, HIV-infected, or other diseased cell is capable of enhancing the SIVA3 level and directly or indirect killing of said cell.

A SIVA3 polypeptide, antibody or a nucleic acid molecule, a SIVA3 binding compound, a vector, or a host cell of the invention can serve as important diagnostic tools. Using these tools assays and kits especially designed for testing SIVA3 can be designed. Examples for reagents in a diagnostic kit or assay include, but are not limited to, antibodies directed to SIVA3, SIVA3 polynucleotide such as SIVA3 specific probes or PCR and sequencing primers allowing detection of SIVA3 expression.

Thus, the invention provides a method and/or kit for diagnosing a disease in a subject comprising assessing the level of expression or activity of SIVA3 polypeptide of the invention in tissue from said subject and comparing said level of expression or activity to a control level. The control level can be the level in a healthy individual. A level of SIVA3 polypeptide or activity in a subject that is different to that of said control level is indicative of disease. Also, the invention provides a similar method for monitoring the therapeutic treatment of disease in a patient by monitoring the level of expression or activity of SIVA3 polypeptide of the invention in tissue from a patient before, after and/or during the therapeutic treatment. A level of SIVA3 polypeptide or activity in a patient after therapeutic treatment that is different to that of the patient before therapeutic treatment is indicative of usefulness of the therapy. The level of expression of SIVA3 polypeptide in the tissue can be measured, for example, by employing: hybridization by a specific probe; specific antibody; or by RT-PCR using specific primers to SIVA3 as shown in the examples below. Using specific methods and kits of the invention, SIVA3 may be used to find association of the levels of SIVA3 with a human disease, disorder or condition that may then be prevented, treated or alleviated by administrating an agent that is capable of regulating the level of SIVA3.

In addition, the invention provides a SIVA3 polypeptide, antibody or a nucleic acid molecule, a SIVA3 modulating compound, a vector, or a host cell of the invention and other compounds capable of altering the activity or level of SIVA3 for use in the manufacture of a medicament for the diagnosis or treatment of a disease, disorder or condition.

Also, the invention provides a method of treating a disease in a patient comprising administering to the patient in need a therapeutically effective amount of a SIVA3 polypeptide, antibody or a nucleic acid molecule, a SIVA3 modulating compound, a vector, or a host cell of the invention and other compounds capable of altering the activity or level of SIVA3. In a further embodiment, the present invention relates to a method for treatment and/or prevention of a disease, disorder or condition caused by or associated with NIK, which comprises administering to a subject in need a therapeutically effective amount of a SIVA3 polypeptide, antibody or a nucleic acid molecule, a SIVA3 binding compound, a vector, or a host cell of the invention and other compounds capable of altering the activity or level of SIVA3. Altering the activity or level of SIVA3 includes increasing or decreasing the activity or level of SIVA3.

An agonist of SIVA3, such as a SIVA3 polypeptide, or a nucleic acid molecule, or a vector, or a host cell, or a compound of the invention capable of increasing the level or the activity of a SIVA3 polypeptide can be used, for example, in a disease disorder or condition in which the expression of a natural gene encoding a SIVA3 polypeptide, or in which the activity of a SIVA3 polypeptide, is lower in a diseased patient when compared to the level of expression or activity in a healthy patient. In contrast, an antagonist of SIVA3, such as antisense nucleic acid molecules, siRNA, ribozymes and ligands, such as antibodies and SIVA3 binding proteins can be used in a disease disorder or condition in which the expression of a natural gene encoding a SIVA3 polypeptide, or in which the activity of a SIVA3 polypeptide, is higher in a diseased patient when compared to the level of expression or activity in a healthy patient.

In one aspect, the invention provides a method of gene therapy for treatment of a disease in which the expression of a natural gene encoding a SIVA3 polypeptide, or in which the activity of a SIVA3 polypeptide, is lower in a diseased patient when compared to the level of expression or activity in a healthy patient or when the activity of NIK or NFκB is higher in a diseased patient when compared to the level of expression or activity in a healthy patient, comprising inducing the expression of SIVA3 or a mutein, fragment at a desired site in a human patient in need by using a polynucleotide encoding a SIVA polypeptide or by Endogenous Gene Activation" (EGA), and it is described e.g. in WO 91/09955.

In another aspect, the invention provides a method of gene therapy for treatment of a disease in which the expression of a natural gene encoding a SIVA3 polypeptide, or in which the activity of a SIVA3 polypeptide, is higher in a diseased patient when compared to the level of expression or activity in a healthy patient or when the activity of NIK or NFkb is lower in a diseased patient when compared to the level of expression or activity in a healthy patient, comprising introducing in diseased cell a specific siRNA, shRNA, a ribozyme, intracellularly expressed antibody, or intrabody, against SIVA3 or any other antagonist of SIVA3.The intrabodies can be prepared as disclosed, for example, in WO 99/14353.

It will be understood by the person skilled in the art that it is possible to shut down SIVA3 expression in order to prevent and/or treat diseases by introducing a negative regulation element, like a specific silencing siRNA, shRNA, a ribozyme, intracellularly leading to downregulation or prevention of SIVA3 expression. The person skilled in the art will understand that such down-regulation or silencing of SIVA3 expression has the same effect as the use of a SIVA3 inhibitor or antagonist.

A therapeutic or diagnostic or research-associated use of some of these tools necessitates their introduction into cells of a living organism. For this purpose, it is desired to improve membrane permeability of peptides, proteins and oligonucleotides. Derivatization with lipophilic structures, may be used in creating peptides and proteins with enhanced membrane permeability. For instance, the sequence of a known membranotropic peptide as noted above may be added to the sequence of the peptide or protein. Further, the peptide or protein may be derivatized by partly lipophilic structures such as the above-noted hydrocarbon chains, which are substituted with at least one polar or charged group. For example, lauroyl derivatives of peptides have been described by Muranishi et al., 1991. Further modifications of peptides and proteins comprise the oxidation of methionine residues to thereby create sulfoxide groups, as described by Zacharia et al. 1991. Zacharia and co-workers also describe peptide or derivatives wherein the relatively hydrophobic peptide bond is replaced by its ketomethylene isoester (COCH2). These and other modifications known to the person of skill in the art of protein and peptide chemistry enhance membrane permeability.

Another way of enhancing membrane permeability is the use receptors, such as virus receptors, on cell surfaces in order to induce cellular uptake of the peptide or protein. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus, see Hemmi et al. 1998, and references therein. The CD4, GPR1, GPR15, and STRL33 molecules have been identified as receptors/co-receptors for HIV, see Edinger et al. 1998 and references therein.

Thus, conjugating peptides, proteins or oligonucleotides to molecules that are known to bind to cell surface receptors will enhance membrane permeability of said peptides, proteins or oligonucleotides. Examples for suitable groups for forming conjugates are sugars, vitamins, hormones, cytokines, transferrin, asialoglycoprotein, and the like molecules. Low et al., U.S. Pat. No. 5,108,921, describes the use of these molecules for the purpose of enhancing membrane permeability of peptides, proteins and oligonucleotides, and the preparation of said conjugates.

Low and co-workers further teach that molecules such as folate or biotin may be used to target the conjugate to a multitude of cells in an organism, because of the abundant and unspecific expression of the receptors for these molecules.

The above use of cell surface proteins for enhancing membrane permeability of a peptide, protein or oligonucleotide of the invention may also be used in targeting said peptide, protein or oligonucleotide of the invention to certain cell types or tissues. For instance, if it is desired to target cancer cells, it is preferable to use a cell surface protein that is expressed more abundantly on the surface of those cells. Examples are the folate receptor, the mucin antigens MUC1, MUC2, MUC3, MUC4, MUC5AC, MUC5B, and MUC7, the glycoprotein antigens KSA, carcinoembryonic antigen, prostate-specific membrane antigen (PSMA), HER-2/neu, and human chorionic gonadotropin-beta. The above-noted Wang et al., 1998, teaches the use of folate to target cancer cells, and Zhang et al. 1998, teaches the relative abundance of each of the other antigens noted above in various types of cancer and in normal cells.

The polypeptide or polynucleotide or compounds of the invention may therefore, using the above-described conjugation techniques, be targeted to certain cell type as desired. For instance, if it is desired to inhibit NIK in cells of the lymphocytic lineage, polypeptide or polynucleotide or compounds of the invention may be targeted at such cells, for instance, by using the MHC class II molecules that are expressed on these cells. This may be achieved by coupling an antibody, or the antigen-binding site thereof, directed against the constant region of said MHC class II molecule to the protein or peptide of the invention. Further, numerous cell surface receptors for various cytokines and other cell communication molecules have been described, and many of these molecules are expressed with in more or less tissue- or cell-type restricted fashion. Thus, when it is desired to target a subgroup of T cells, the CD4 T cell surface molecule may be used for producing the conjugate of the invention. CD4-binding molecules are provided by the HIV virus, whose surface antigen gp42 is capable of specifically binding to the CD4 molecule.

In one embodiment, peptides and polynucleotides may be introduced into cells by the use of a viral vector. The use of vaccinia vector for this purpose is detailed in chapter 16 of Current Protocols in Molecular Biology. The use of adenovirus vectors has been described e.g. by Teoh et al. (Blood. 1998 Dec. 15; 92(12):4591-601), Narumi et al, 1998 (Blood. 1998 Aug. 1; 92(3):822-33; and Am J Respir Cell Mol Biol. 1998 December; 19(6):936-41), Pederson et al, 1998 (J Gastrointest Surg. 1998 May-June; 2(3):283-91), Guang-Lin et al., 1998 (Transplant Proc. 1998 November; 30(7):2923-4), and references therein, Nishida et al., 1998 (Spine. 1998 Nov. 15; 23(22):2437-42; discussion 2443), Schwarzenberger et al 1998 (J Immunol. 1998 Dec. 1; 161(11):6383-9), and Cao et al., 1998 (Gene Ther. 1998 August; 5(8):1130-6.). Retroviral transfer of antisense sequences has been described by Daniel et al. 1998 (J Biomed Sci. 1998 September-October; 5(5): 383-94.).

When using viruses as vectors, the viral surface proteins are generally used to target the virus. As many viruses, such as the above adenovirus, are rather unspecific in their cellular tropism, it may be desirable to impart further specificity by using a cell-type or tissue-specific promoter. Griscelli et al., 1998 teach the use of the ventricle-specific cardiac myosin light chain 2 promoter for heart-specific targeting of a gene whose transfer is mediated by adenovirus.

Alternatively, the viral vector may be engineered to express an additional protein on its surface, or the surface protein of the viral vector may be changed to incorporate a desired peptide sequence. The viral vector may thus be engineered to express one or more additional epitopes, which may be used to target, said viral vector. For instance, cytokine epitopes, MHC class II-binding peptides, or epitopes derived from homing molecules may be used to target the viral vector in accordance with the teaching of the invention.

In a further aspect, the invention provides a pharmaceutical composition comprising a SIVA3 polypeptide, antibody or a nucleic acid molecule, a SIVA3 binding compound, a vector, or a host cell of the invention and other compounds capable of altering the activity or level of SIVA3 and a pharmaceutically acceptable carrier.

The pharmaceutical composition according to the present invention includes a therapeutically effective amount of polypeptides, polynucleotide a SIVA3 binding compound according to the invention to achieve its intended purpose. In addition, the pharmaceutical compositions may contain suitable pharmaceutically acceptable carriers comprising excipients and auxiliaries such as pharmaceutically acceptable surfactants, excipients, carriers, diluents and vehicles which facilitate processing of the active compounds into preparations and can stabilize such preparations, as well-known in the art.

The compositions according to the invention can be administered to a patient in a variety of ways. Any suitable route of administration is envisaged by the invention such as, but not limited to, intraliver, intradermal, transdermal (e.g. in slow release formulations), intramuscular, intraperitoneal, intravenous, subcutaneous, oral, epidural, topical, and intranasal routes. The composition can be administered together with other biologically active agents.

The definition of "pharmaceutically acceptable" is meant to encompass any carrier, which does not interfere with effectiveness of the biological activity of the active ingredient and that is not toxic to the host to which it is administered. For example, for parenteral administration, the substance according to the invention may be formulated in a unit dosage form for injection in vehicles such as saline, dextrose solution, serum albumin and Ringer's solution.

A "therapeutically effective amount" is such that when administered, the said substances of the invention induce a beneficial effect in therapy. The dosage administered, as single or multiple doses, to an individual may vary depending upon a variety of factors, including the route of administration, patient conditions and characteristics (sex, age, body weight, health, and size), extent and severity of symptoms, concurrent treatments, frequency of treatment and the effect desired. Adjustment and manipulation of established dosage ranges are well within the ability of those skilled in the art.

The term "dosage" relates to the determination and regulation of the frequency and number of doses.

All references cited herein, including articles or abstracts, published or unpublished patent application, issued patents or any other references, are entirely incorporated by reference herein.

The invention will be now illustrated by the following non-limiting examples.

EXAMPLES

Material and Methods

Antibodies: Antibody against p52 was purchased from upstate anti p52 recognizes both p52 and p100. anti-FLAG, anti-FLAG M2-beads, was purchased from Sigma. The anti-NIK monoclonal antibody NIK-81 was raised by immunizing mice with a KLH-coupled peptide corresponding to a sequence within the NIK kinase domain (CRLGRGSFGEV-HRMEDK-amino acids 405-420 SEQ ID NO: 7). Anti-NIK, and anti-myc (clone-9E10) monoclonal antibodies were purified from mouse ascitic fluids on affinity columns to which their corresponding peptides were coupled. anti-cIAP1 was purchased from R&D systems. A monoclonal antibody against human SIVA2 was raised in mice by their immunization with bacterially produced GST-SIVA2 and was affinity-purified with Trx-HIS-SIVA2. This antibody recognized both SIVA1 and SIVA2.

Mammalian Expression Vectors

SIVA3 was cloned from peripheral blood mononuclear cells by PCR. SIVA2 was cloned from EST by PCR. The SIVA sequence was verified with the NCBI sequence NM_021709 (SIVA2). pCS3MTNIK expression vectors for wild-type NIK fused N-terminally to a six myc tag, were obtained from Dr. Michael Kracht, Germany. Flag-SIVA2, Flag-SIVA3, HIS-SIVA3 and Flag-TRAF2 were cloned in pcDNA3 expression vector (Invitrogen).

Semiquantitative RT-PCR and Real-Time PCR.

RNA was prepared using the RNeasy Mini Kit (Qiagen) according to the manufacturer's instructions. Semiquantitative RT-PCR for SIVA2 message was performed with MMLV reverse transcriptase and oligo dT primer (Promega). SIVA1, SIVA2, and SIVA3 were amplified by use of the following primers: sense strand 5'-cgcggatccaacatgcccaagcggagct-gcccc-3' (SEQ ID NO: 8), which contains a BamHI site, and antisense strand 5'-ccgctcgaggccagcctcaggtctcgaacatgg-3' (SEQ ID NO: 9), which contains a XhoI site. Induction of IL-6 and BLC messages was quantified by Assays-on-Demand Real-Time PCR in an ABI PRISM 7000 Sequence Detection System. The primer sequences used for the PCR amplification in FIG. 1A are:

forward:
CGCGGATCCACCATGCCCAAGCGGAGCTGCCCC, (SEQ ID NO: 3)

reverse:
CCGCTCGAGGCCAGCCTCAGGTCTCGAACATGG. (SEQ ID NO: 4)

Primers used for the PCR amplification of full length SIVA3 (FIG. 1B) are:

Forward:
CGCGGATCCACCATGCCCAAGCGGAGCTGCCCC (SEQ ID NO: 5)

Reverse:
CCGCTCGAGAGAGGTTTATTCATTCTGTCATTAGG (SEQ ID NO: 6)

Forward primer is designed with a BamHI site before start codon and the reverse primer with a XhoI site is designed. At the first stop codon arising from the frame shift down stream of the real stop codon.

Cells

The adherent cells HEK-293T and HeLa (FIG. 4) were cultured in Dulbecco's modified Eagle's medium. Both culture media were supplemented with 10% fetal calf serum, 100 U/ml pencillin, and 100 µg/ml streptomycin.

Plasmid Transfections, Immunoblotting, and Immunoprecipitations:

Immunoblotting and immunoprecipitations were performed as described (Ramakrishnan et al., 2004).

Immunoblotting and immunoprecipitations were performed as described (Ramakrishnan et al., 2004). Typically, $1.5 \times 10^6$ cells were seeded into 10 cm plates. Following a 24 hr period of incubation the cultures were transfected with respective plasmids while maintaining a total DNA concentration of 15 µg per plate by adding empty vector.

Typically, cells were seeded onto 90-mm plates ($1.5 \times 10^6$ cells/plate) and transfected using the calcium phosphate precipitation method (Sambrook et al., 1989) a day later using a total amount of 10 µg DNA in 10 ml of DMEM medium with 10% FBS. For co-transfection a 1:1 mixture of the plasmids encoding tested proteins was used unless otherwise specified. Twenty four hours following transfection the cells were rinsed once with phosphate buffered saline (PBS) and lysed in 1 ml of lysis buffer (10 mM Tris-HCl (pH 7.6), 250 mM NaCl, 1% NP-40, 1 mM EDTA, 1 mM PMSF) which included 1× complete protease inhibitor cocktail (Roche Molecular Biochemicals). Pre-cleared lysates were incubated for 2 hours at 4° C. with 2 µg of anti-myc or anti-HIS antibody preabsorbed to protein-G-Sepharose beads (Amersham biosciences). The beads were then rinsed with lysis buffer, subjected to SDS-PAGE, and the proteins were transferred to a nitrocellulose membrane and probed with the indicated antibodies. The antibodies were visualized with horseradish peroxidase (HRP)-coupled secondary antibodies, using the enhanced chemiluminescence (ECL) Western blotting detection system (Amersham) according to the manufacturer's instructions.

To prepare lysate of cells, typically, cells were harvested 24 hr following transfection then lysed in 1% Triton X-100 lysis buffer [(1% Triton X-100, 150 mM NaCl, 1 mM EDTA, 20 mM Tris-cl (pH 7.6) and 1× complete protease inhibitor (Roche)]. All immunoprecipitations were carried out by incubation for 4 hours at 4° C. with the specific antibodies and protein G sepharose beads (Amersham Pharmacia).

Lysis condition differs where nuclear and cytoplasmic extract are separated (Schreiber et al., 1989).

Example 1:

Identification of SW A3, an Endogenous SIVA Splice Variant

On closer examination of SIVA expression by PCR (PCR conditions: denaturation 94 degrees 3 min, annealing 50 degrees 1 min, extension 72 degrees 1 min. Final extension 5 min. Total 35 cycles) in peripheral-blood mononuclear cells (PBMCs), transcripts of both splice variants SIVA1 and SIVA2 were found as well of a yet shorter variant (named herein 'SIVA3') (FIG. 1A). The full size SIVA3 transcript was amplified (FIG. 1B).

The nucleotide sequence of SIVA3 (SEQ ID NO:2 and FIG. 2)T was identified by sequencing the PCR product cloned in pcDNAHISc vector (Invitrogen), in the Weizmann Institute of Science DNA sequencing facility and amino acid of SIVA3 (SEQ ID NO:1 and FIG. 3) was deduced by translating the DNA sequence obtained in the software DNA strider. SIVA3 sequence was found to be about 35% (39 amino acids of 110) identical to SIVA2 and less (about 22%, 39 of 175 amino acids) to SIVA1. The SIVA3 transcript comprised exons 1 and 4 of SIVA1 and SIVA2, but with a frame shift at the junction of exon 1 and exon 4, which resulted in reading through the original stop codon at the end of exon 4 adding additional 68 amino acids from the 3' non-coding region of SIVA.

The deposit No. of SIVA 3 at the CNCM (Collection Nationale de Cultures de Microorganismes, at address INSTITUT PASTEUR, 25 rue du Docteur Roux, F-75724 PARIS Cedex 15) is CNCM I-3880. The deposit was received by CNCM on Dec. 13, 2007.

Example 2

SIVA3 Induces Degradation of NIK and Inhibition of NF-κB Activation

The function of SIVA3 was further explored. For this purpose, myc-NIK expression vector (0.5 ug) was transfected with increasing concentrations of FLAG-SIVA3 expression vector (1.5 ug and 3.0 ug)) in HeLa cells. 30 h post transfection cells were harvested and the cellular levels of NIK and p100/p52 were assessed by western blotting.

Figure 4:
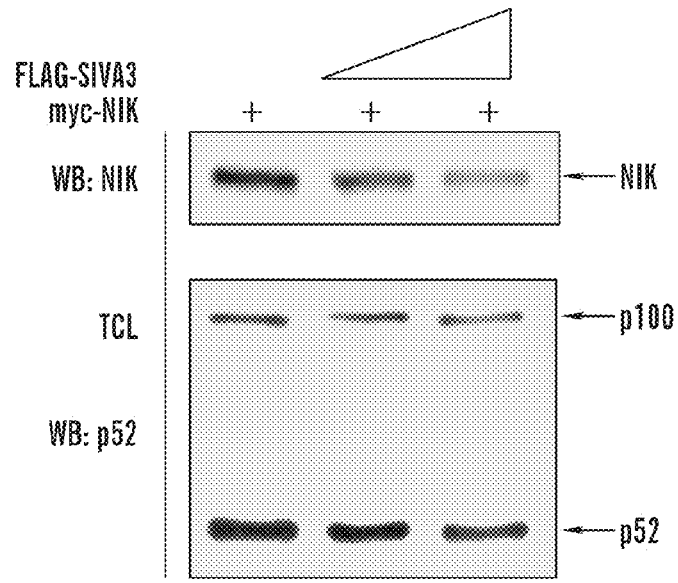
FIG. 4 shows effect of increased SIVA3 expression on the levels of NIK, p100 and p52 in cells. Myc tagged-NIK expression vector was co-transfected with increasing concentrations of FLAG-SIVA3 expression vector in HeLa cells and cellular levels of NIK and p100/p52 was assessed in the cells 30 h post transfection. WB=Western Blot, TLC=Total cell lysate.

The results summarized in FIG. 4 show that the increase in SIVA3 levels induces degradation of NIK and inhibition of activation of NF-κB mediated by NIK as reflected by the reduction of active processing of p100 to form p52.

Figure 5:
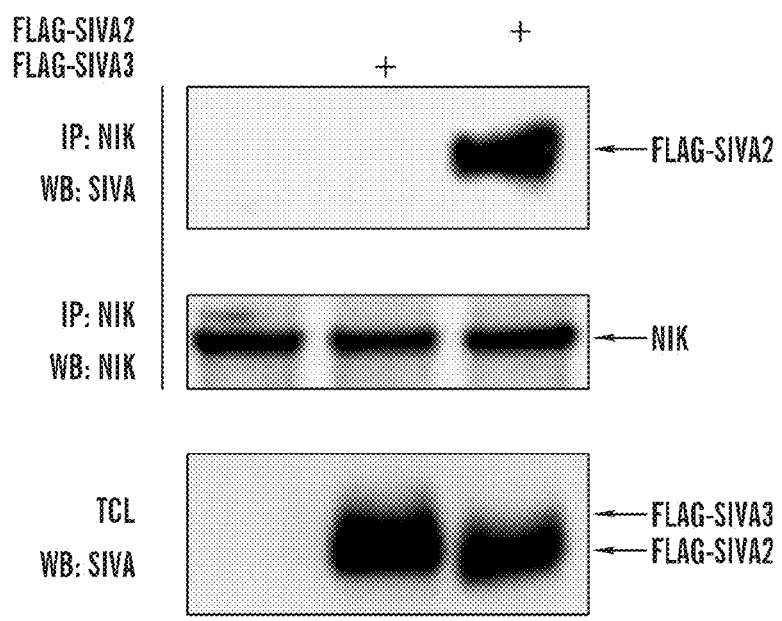
FIG. 5 shows that SIVA3 does not coimmunoprecipitate with NIK. FLAG-SIVA2 or FLAG-SIVA3 expression vectors were co-transfected with NIK expression vector into HEK-293T cells. 24 h later, cells were lysed, NIK was immunoprecipitated with anti-NIK antibody and co-precipitated SIVA was monitored by western Blotting. WB=Western Blot, TLC=Total cell lysate, IP=immunoprecipitation.

Next, it was explored whether SIVA3 binds NIK. FLAG-SIVA2 (8 µg) or FLAG-SIVA3 (8 µg) were co-transfected with myc-NIK (7 µg) into HEK-293T cells ($1.5 \times 10^6$ seeded in 90 mm plate, transfected using calcium phosphate method). 24 h later, cells were lysed, NIK was immunoprecipitated with anti-NIK antibody and co-precipitated SIVA was detected by western Blotting. The results in FIG. 5 show that SIVA3 does not bind to NIK.

Example 3

SIVA3 Binds an Endogenous Cellular Inhibitor of Apoptosis Protein 1 (cIAP1)

Next, it was tested whether SIVA2 and SIVA3 can bind an endogenous cellular inhibitor of apoptosis protein 1 (cIAP1). For this purpose FLAG-SIVA2 and FLAG-SIVA3 were transfected into HEK-293T cells. 24 h later, cells were lysed, endogenous cIAP1 was immunoprecipitated with anti-cIAP1 antibody and co-precipitated SIVA was detected by Western blotting.

Figure 6:
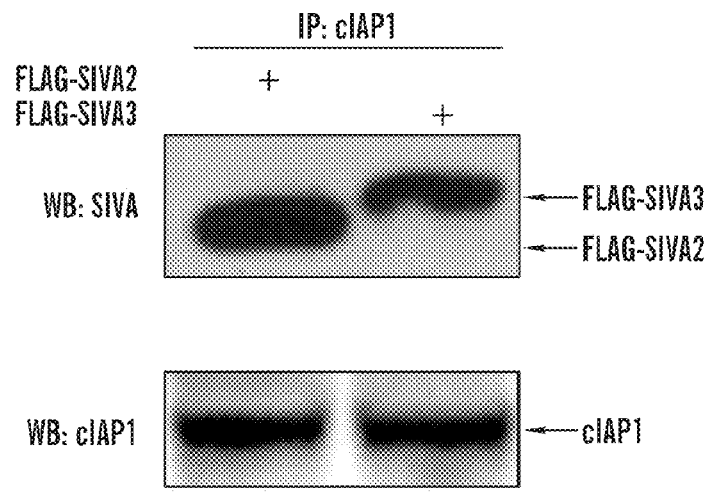
FIG. 6 shows that SIVA2 and SIVA3 coimunoprecipitate with endogenous cellular inhibitor of apoptosis protein 1 (cIAP1). FLAG-SIVA2 or FLAG-SIVA3 expression vectors were transfected into HEK-293T cells. 24 h later, cells were lysed, endogenous cIAP1 was immunoprecipitated with anti-cIAP1 antibody and co-precipitated SIVA was detected by western Blotting
Figure 7:
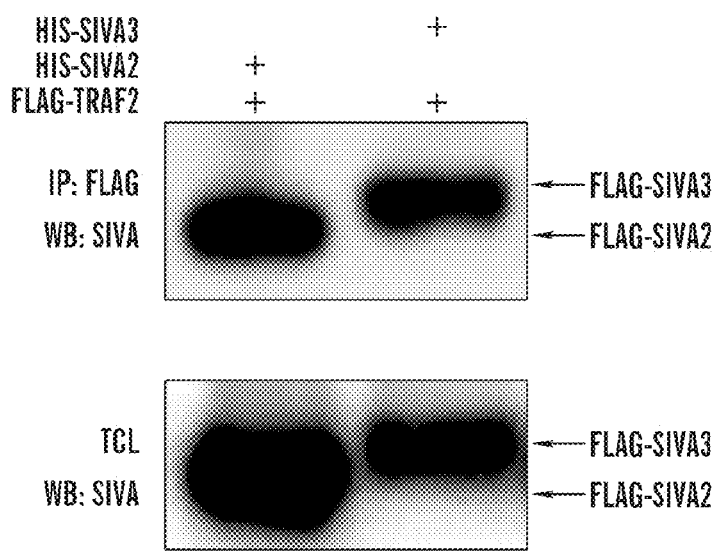
FIG. 7 shows that HIS-SIVA2 or HIS-SIVA3 were co-transfected with FLAG-TRAF2 into HEK-293T cells. 24 h later, cells were lysed, FLAG-TRAF2 was immunoprecipitated with anti-FLAG antibody and co-precipitated SIVA was detected by western blotting.

The results summarized in FIGS. 6 and 7 demonstrate that both, SIVA2 and SIVA3 bind to cIAP1.

Example 4

SIVA3 Binds to TRAF2

Since the applicants of this invention found that SIVA2 binds and regulates TRAF2 levels (WO2007080593), it was explored whether SIVA3 can also bind TRAF2. For this purpose HIS-SIVA2 or HIS-SIVA3 expression plasmids was co-transfected with FLAG-TRAF2 into HEK-293T cells. 24 h later, cells were lysed, FLAG-TRAF2 was immunoprecipitated with anti-FLAG antibody and co-precipitated SIVA was detected by Western blotting using anti HIS. The results summarized in FIGS. 8 and 9 show that SIVA3 binds to TRAF2.

References

Canicio, J., Ruiz-Lozano, P., Carrasco, M., Palacin, M., Chien, K., Zorzano, A., and Kaliman, P. (2001). Nuclear factor kappa B-inducing kinase and Ikappa B kinase-alpha signal skeletal muscle cell differentiation. J Biol Chem 276, 20228-20233.

Cao, C., Ren, X., Kharbanda, S., Koleske, A., Prasad, K. V., and Kufe, D. The ARG tyrosine kinase interacts with Siva-1 in the apoptotic response to oxidative stress. J Biol Chem 276, 11465-11468. 2001

Chu, F., Barkinge, J., Hawkins, S., Gudi, R., Salgia, R., and Kanteti, P. V. Expression of Siva-1 protein or its putative amphipathic helical region enhances cisplatin-induced apoptosis in breast cancer cells: effect of elevated levels of BCL-2. Cancer Res 65, 5301-5309. 2005

Chu, F., Borthakur, A., Sun, X., Barkinge, J., Gudi, R., Hawkins, S., and Prasad, K. V. The Siva-1 putative amphipathic helical region (SAH) is sufficient to bind to BCL-XL and sensitize cells to UV. 2004

Collins and Cybulsky, 2001. J Clin Invest. 108:255-64.

Deng, L., Wang, C., Spencer, E., Yang, L., Braun, A., You, J., Slaughter, C., Pickart, C., and Chen, Z. J. Activation of the IkappaB kinase complex by TRAF6 requires a dimeric ubiquitin-conjugating enzyme complex and a unique polyubiquitin chain. Cell 103, 351-361.98. 2000

Dorsett, Y. and T. Tuschl (2004). "siRNAs: applications in functional genomics and potential as therapeutics." Nat Rev Drug Discov 3(4): 318-29.

Edinger et al. 1998 Virology. 1998 Sep. 30; 249(2):367-78

Fanslow, W. C., Clifford, K. N., Seaman, M., Alderson, M. R., Spriggs, M. K., Armitage, R. J., and Ramsdell, F. Recombinant CD40 ligand exerts potent biologic effects on T cells. J Immunol 152, 4262-4269. 1994

Foehr, E. D. et al., 2000. J Biol Chem. 275:34021-4

Fontanari Krause et al, Abstract 3152, Blood, Vol: 102, 11, Nov. 16, 2003.

Fortin, A., MacLaurin, J. G., Arbour, N., Cregan, S. P., Kushwaha, N., Callaghan, S. M., Park, D. S., Albert, P. R., and Slack, R. S. The proapoptotic gene SIVA is a direct transcriptional target for the tumor suppressors p53 and E2F 1. J Biol Chem 279, 28706-28714. 2004

Fred M. Ausubel, R. B., Robert E. Kingston, David D. Moore, J. G. Seidman, John A. Smith, Kevin Struhl, ed. Current protocols in molecular biology. 1996

Glickman, M. H., and Ciechanover, A. The ubiquitin-proteasome proteolytic pathway: destruction for the sake of construction. Physiol Rev 82, 373-428. 2002

Grech, A. P., Amesbury, M., Chan, T., Gardam, S., Basten, A., and Brink, R. TRAF2 differentially regulates the canonical and noncanonical pathways of NF-kappaB activation in mature B cells. Immunity 21, 629-642. 2004

Hemmi et al. 1998 Hum Gene Ther. 1998 Nov. 1; 9(16): 2363-73

Henke, A., Launhardt, H., Klement, K., Stelzner, A., Zell, R., and Munder, T. Apoptosis in coxsackievirus B3-caused diseases: interaction between the capsid protein VP2 and the proapoptotic protein siva. J Virol 74, 4284-4290. 2000

Hofmann, K., and Falquet, L. A ubiquitin-interacting motif conserved in components of the proteasomal and lysosomal protein degradation systems. Trends Biochem Sci 26, 347-350. 2001

Hofmann, R. M., and Pickart, C. M. In vitro assembly and recognition of Lys-63 polyubiquitin chains. J Biol Chem 276, 27936-27943. 2001

Kajiura, F., Sun, S., Nomura, T., Izumi, K., Ueno, T., Bando, Y., Kuroda, N., Han, H., Li, Y., Matsushima, A., et al. (2004). NF-kappa B-inducing kinase establishes self-tolerance in a thymic stroma-dependent manner. J Immunol 172, 2067-2075.

Karin, M., and Ben-Neriah, Y. Phosphorylation meets ubiquitination: the control of NF-[kappa]B activity. Annu Rev Immunol 18, 621-663. 2000

Kim, D. H., M. A. Behlke, et al. (2005). "Synthetic dsRNA Dicer substrates enhance RNAi potency and efficacy." Nat Biotechnol 23(2): 222-6.

Kovalenko, A., Chable-Bessia, C., Cantarella, G., Israel, A., Wallach, D., and Courtois, G. The tumour suppressor CYLD negatively regulates NF-kappaB signalling by deubiquitination. Nature 424, 801-805. 2003

Lee, Z. H., Lee, S. E., Kwack, K., Yeo, W., Lee, T. H., Bae, S. S., Suh, P. G., and Kim, H. H. Caspase-mediated cleavage of TRAF3 in FasL-stimulated Jurkat-T cells. J Leukoc Biol 69, 490-496. 2001

Leonard, W. J. et al., 1995. Immunol Rev. 148:97-114.

Liao, G., Zhang, M., Harhaj, E. W., and Sun, S. C. Regulation of the NF-kappaB-inducing kinase by tumor necrosis factor receptor-associated factor 3-induced degradation. J Biol Chem 279, 26243-26250. 2004

Lin, X. et al., 1999. Immunity 10:271-80.

Ling, L. et al., 1998. Proc Natl Acad Sci USA. 95:3792-7

Lois, C., Hong, E. J., Pease, S., Brown, E. J., and Baltimore, D. Germline transmission and tissue-specific expression of transgenes delivered by lentiviral vectors. Science 295, 868-872. 2002.

Malinin, N. L., Boldin, M. P., Kovalenko, A. V., and Wallach, D. MAP3K-related kinase involved in NF-kappaB induction by TNF, CD95 and IL-1. Nature 385, 540-544. 1997.

Matsushima, A. et al., 2001. J Exp Med. 193:631-6.

Matsushima, A. et al., 2001. J Exp Med. 193:631-6

Matsumoto, M. et al., 1999. J Immunol. 163:1584-91.

Mattson and Camandola, 2001. J Clin Invest. 107:247-54.

Mercurio F. and Manning A. M., 1999. Curr Opin Cell Biol. 11:226-32.

Miyawaki, S., Nakamura, Y., Suzuka, H., Koba, M., Yasumizu, R., Ikehara, S., and Shibata, Y. (1994). A new mutation, aly, that induces a generalized lack of lymph nodes accompanied by immunodeficiency in mice. Eur J Immunol 24, 429-434.

Muranishi et al., 1991 Lipophilic peptides: synthesis of lauroyl thyrotropin-releasing hormone and its biological activity. Pharm Res. 1991 May; 8(5):649-52

Nocentini, G., and Riccardi, C. GITR: a multifaceted regulator of immunity belonging to the tumor necrosis factor receptor superfamily. Eur J Immunol 35, 1016-1022. 2005

Padanilam, B. J., Lewington, A. J., and Hammerman, M. R. Expression of CD27 and ischemia/reperfusion-induced expression of its ligand Siva in rat kidneys. Kidney Int 54, 1967-1975. 1998

Petit P X, P. B., Mrugala D, Biard-Piechaczyk M, Benichou S. SIVA: A new intracellular ligand of the CD4 receptor modulating T lymphocyte apoptosis via a caspase-dependent mitochondrial pathway, Paper presented at: ISAC congress XXII (France: WILEY-LISS, DIV JOHN WILEY & SONS INC, 111 RIVER ST, HOBOKEN, N.J. 07030 USA). 2004

Pickart, C. M. Mechanisms underlying ubiquitination. Annu Rev Biochem 70, 503-533. 2001

Pomerantz, J. L., and Baltimore, D. (2002). Two pathways to NF-kappaB. Mol Cell 10, 693-695.

Prasad, K. V., Ao, Z., Yoon, Y., Wu, M. X., Rizk, M., Jacquot, S., and Schlossman, S. F. CD27, a member of the tumor necrosis factor receptor family, induces apoptosis and binds to Siva, a proapoptotic protein. Proc Natl Acad Sci USA 94, 6346-6351. 1997

Prasad, K. V., Ao, Z., Yoon, Y., Wu, M. X., Rizk, M., Jacquot, S., and Schlossman, S. F. (1997). CD27, a member of the tumor necrosis factor receptor family, induces apoptosis and binds to Siva, a proapoptotic protein. Proc Natl Acad Sci USA 94, 6346-6351.

Py, B., Slomianny, C., Auberger, P., Petit, P. X., and Benichou, S. Siva-1 and an alternative splice form lacking the death domain, Siva-2, similarly induce apoptosis in T lymphocytes via a caspasedependent mitochondrial pathway. J Immunol 172, 4008-4017. 2004

Qin, L. F., Lee, T. K., and Ng, I. O. Gene expression profiling by cDNA array in human hepatoma cell line in response to cisplatin treatment. Life Sci 70, 1677-1690. 2002

Ramakrishnan, P., Wang, W., and Wallach, D. Receptor-specific signaling for both the alternative and the canonical NF-kappaB activation pathways by NF-kappaB-inducing kinase. Immunity 21, 477-489. 2004

Regnier, C. H. et al., 1997. Cell 90:373-83.

Rigaut, G., Shevchenko, A., Rutz, B., Wilm, M., Mann, M., and Seraphin, B. A generic protein purification method for protein complex characterization and proteome exploration. Nat Biotechnol 17, 1030-1032. 1999

Schreiber, E., Matthias, P., Muller, M. M., and Schaffner, W. Rapid detection of octamer binding proteins with 'mini-extracts', prepared from a small number of cells. Nucleic Acids Res 17, 6419. 1989

Senftleben, U., Cao, Y., Xiao, G., Greten, F. R., Krahn, G., Bonizzi, G., Chen, Y., Hu, Y., Fong, A., Sun, S. C., and Karin, M. Activation by IKKalpha of a second, evolutionary conserved, NF-kappa B signaling pathway. Science 293, 1495-1499. 2001

Shinkura, R., Kitada, K., Matsuda, F., Tashiro, K., Ikuta, K., Suzuki, M., Kogishi, K., Serikawa, T., and Honjo, T. Alymphoplasia is caused by a point mutation in the mouse gene encoding Nf-kappa binducing kinase. Nat Genet 22, 74-77.107. 1999

Spinicelli, S., Nocentini, G., Ronchetti, S., Krausz, L. T., Bianchini, R., and Riccardi, C. GITR interacts with the pro-apoptotic protein Siva and induces apoptosis. Cell Death Differ 9, 1382-1384. 2002

Sylla, B. S. et al., 1998. Proc Natl Acad Sci USA. 95:10106-11

Soutschek, J., A. Akinc, et al. (2004). "Therapeutic silencing of an endogenous gene by systemic administration of modified siRNAs." Nature 432(7014): 173-8.

Spinicelli, S., Nocentini, G., Ronchetti, S., Krausz, L. T., Bianchini, R., and Riccardi, C. GITR interacts with the pro-apoptotic protein Siva and induces apoptosis. Cell Death Differ 9, 1382-1384. 2002

Wajant, H., and Scheurich, P. (2004). Analogies between *Drosophila* and mammalian TRAF pathways. Prog Mol Subcell Biol 34, 47-72.

Wang et al., 1998 J Control Release. 1998 Apr. 30; 53(1-3):39-48. Review

Xiao, G., Fong, A., and Sun, S. C. Induction of p100 processing by NF-kappaB-inducing kinase involves docking IkappaB kinase alpha (IKKalpha) to p100 and IKKalpha-mediated phosphorylation. J Biol Chem 279, 30099-30105. 2004

Xiao, G., and Sun, S. C. Negative regulation of the nuclear factor kappa B-inducing kinase by a cis-acting domain. J Biol Chem 275, 21081-21085. 2000

Xu, L. G., Li, L. Y., and Shu, H. B. (2004). TRAF7 potentiates MEKK3-induced AP1 and CHOP activation and induces apoptosis. J Biol Chem 279, 17278-17282.

Xue, L., Chu, F., Cheng, Y., Sun, X., Borthakur, A., Ramarao, M., Pandey, P., Wu, M., Schlossman, S. F., and Prasad, K. V. Siva-1 binds to and inhibits BCL-X(L)-mediated protection against UV. 2002

Yamamoto and Gaynor, 2001. J Clin Invest. 107:135-142

Yoon, Y., Ao, Z., Cheng, Y., Schlossman, S. F., and Prasad, K. V. Murine Siva-1 and Siva-2, alternate splice forms of the mouse Siva gene, both bind to CD27 but differentially transduce apoptosis. Oncogene 18, 7174-7179. 1999

Zacharia et al. 1991 Eur J Pharmacol. 1991 Oct. 22; 203 (3):353-7.

Zhang et al. 1998 Clin Cancer Res. 1998 November; 4(11): 2669-76. and Clin Cancer Res. 1998 February; 4(2):295-302

---

The invention claimed is:

1. An isolated polynucleotide encoding a Siva3 polypeptide, said polynucleotide having the sequence of SEQ ID NO:2.

2. A vector comprising a polynucleotide sequence according to claim 1.

3. A host cell comprising a vector according to claim 2.

4. The host cell according to claim 3, wherein the cell is a eukaryotic cell.

5. The host cell according to claim 4, wherein the eukaryotic cell is a mammalian cell selected from HeLa, 293 T HEK and CHO cells.

6. A pharmaceutical composition comprising a pharmaceutically acceptable carrier and:
   a) a polynucleotide encoding a signal peptide for secretion operably linked to a Siva3 polypeptide, said polynucleotide having the sequence of SEQ ID NO:2;
   b) a vector comprising the polynucleotide of (a); or
   c) a mammalian host cell comprising the vector of (b).

7. A clone of deposit number CNCM I-3880 having the sequence of SEQ ID NO: 2.

* * * * *

SEQUENCE LISTING

```
<160> NUMBER OF SEQ ID NOS: 9

<210> SEQ ID NO 1
<211> LENGTH: 107
<212> TYPE: PRT
<213> ORGANISM: Homo sapiens

<400> SEQUENCE: 1

Met Pro Lys Arg Ser Cys Pro Phe Ala Asp Val Ala Pro Leu Gln Leu
1               5                   10                  15

Lys Val Arg Val Ser Gln Arg Glu Leu Ser Arg Gly Val Cys Ala Glu
            20                  25                  30
```

```
Arg Tyr Ser Gln Glu Val Phe Ala Ala Val Thr Cys Thr Arg Lys Cys
         35                  40                  45

Cys Ala Pro Ala Val Pro Cys Ser Arg Pro Glu Ala Gly Ser Ser Arg
 50                  55                  60

Leu Pro Ser Pro Gly Ala Thr Pro Cys Met Ala Phe Pro Gly Arg
 65                  70                  75                  80

Ala Leu Gly Val His Thr Glu Leu Trp Gly Arg Arg Glu Gly Cys Leu
                 85                  90                  95

Leu His Val Leu Phe Cys Ile Leu Met Thr Glu
                100                 105
```

```
<210> SEQ ID NO 2
<211> LENGTH: 324
<212> TYPE: DNA
<213> ORGANISM: Homo sapiens

<400> SEQUENCE: 2
atgcccaagc ggagctgccc cttcgcggac gtggccccgc tacagctcaa ggtccgcgtg      60
agccagaggg agttgagccg cggcgtgtgc gccgagcgct actcgcagga ggtcttcgct     120
gcagtgacat gtacgagaaa gtgctgtgca ccagctgtgc catgttcgag acctgaggct     180
ggctcaagcc ggctgccttc accgggagcc acgccgtgca tggcagcctt ccctggacga     240
gcgctcggtg ttcacactga actgtggggt cgacgggagg ggtgcctttt acatgttcta     300
ttttgtatcc taatgacaga atga                                           324
```

```
<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcggatcca ccatgcccaa gcggagctgc ccc                                   33
```

```
<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgctcgagg ccagcctcag gtctcgaaca tgg                                   33
```

```
<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcggatcca ccatgcccaa gcggagctgc ccc                                   33
```

```
<210> SEQ ID NO 6
<211> LENGTH: 35
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 6
ccgctcgaga gaggtttatt cattctgtca ttagg                                35

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      NIK kinase domain peptide

<400> SEQUENCE: 7

Cys Arg Leu Gly Arg Gly Ser Phe Gly Glu Val His Arg Met Glu Asp
1               5                   10                  15

Lys

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgcggatcca acatgcccaa gcggagctgc ccc                                  33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgctcgagg ccagcctcag gtctcgaaca tgg                                  33
```